(12) United States Patent
Chorlton et al.

(10) Patent No.: US 8,779,146 B2
(45) Date of Patent: Jul. 15, 2014

(54) CILOSTAZOL COCRYSTALS AND COMPOSITIONS

(75) Inventors: Alan Chorlton, Newmarket (GB);
Christopher Frampton, Suffolk (GB);
Daniel Gooding, Cambridge (GB);
Joanne Holland, Histon (GB)

(73) Assignee: Nuformix Limited (GB)

( * ) Notice: Subject to any disclaimer, the term of this patent is extended or adjusted under 35 U.S.C. 154(b) by 0 days.

(21) Appl. No.: 13/643,213

(22) PCT Filed: Apr. 28, 2011

(86) PCT No.: PCT/IB2011/001430
§ 371 (c)(1),
(2), (4) Date: Mar. 19, 2013

(87) PCT Pub. No.: WO2011/158110
PCT Pub. Date: Dec. 22, 2011

(65) Prior Publication Data
US 2013/0203806 A1    Aug. 8, 2013

Related U.S. Application Data

(60) Provisional application No. 61/452,363, filed on Mar. 14, 2011, provisional application No. 61/328,827, filed on Apr. 28, 2010.

(51) Int. Cl.
*A61K 31/04* (2006.01)
*C07D 215/04* (2006.01)
*C07D 215/20* (2006.01)
*A61K 31/4709* (2006.01)

(52) U.S. Cl.
CPC ........... *C07D 215/20* (2013.01); *A61K 31/4709* (2013.01)
USPC .......................................... 546/159; 514/312

(58) Field of Classification Search
CPC ............. C07D 215/227; C07D 215/20; A61K 31/4709
USPC .......................................... 546/159; 514/312
See application file for complete search history.

(56) References Cited

U.S. PATENT DOCUMENTS

| | | |
|---|---|---|
| 4,277,479 A | 7/1981 | Nishi et al. |
| 6,187,790 B1 | 2/2001 | Cutler |
| 6,515,128 B2 | 2/2003 | Mendelovici et al. |
| 6,525,201 B2 | 2/2003 | Mendelovici et al. |
| 6,531,603 B1 | 3/2003 | Stowell et al. |
| 6,573,382 B2 | 6/2003 | Stowell et al. |
| 6,657,061 B2 | 12/2003 | Stowell et al. |
| 6,660,773 B2 | 12/2003 | Mendelovici et al. |
| 6,660,864 B2 | 12/2003 | Stowell et al. |
| 6,740,758 B2 | 5/2004 | Mendelovici et al. |
| 6,825,214 B2 | 11/2004 | Mendelovici et al. |
| 2009/0297596 A1 | 12/2009 | Devane et al. |

FOREIGN PATENT DOCUMENTS

| | | |
|---|---|---|
| CN | 101287451 A | 10/2008 |
| JP | 56-49378 A | 5/1981 |
| WO | 2004/078163 A2 | 9/2004 |
| WO | 2005/055983 A2 | 6/2005 |
| WO | 2006/121249 A1 | 11/2006 |
| WO | 2008/030209 A2 | 3/2008 |
| WO | 2009/107864 A2 | 9/2009 |
| WO | 2009/133741 A2 | 9/2009 |
| WO | 2011/158110 A2 | 12/2011 |

OTHER PUBLICATIONS

Yamamoto, Int J Pharm, vol. 437, pp. 162-171, 2012.*
Schultheiss et al., "Pharmaceutical Cocrystals and Their Physicochemical Properties", Crystal Growth & Design, vol. 9, No. 6, Jun. 3, 2009, pp. 2950-2967.
Search Report and Written Opinion of PCT International Application No. PCT/IB2011/001430, dated Jan. 25, 2012.
Nishi et al., "Studies on 2-Oxoquinoline Derivatives as Blood Platelet Aggregation Inhibitors. II. 6-[3-(1-Cyclohexyl-5-tetrazolyl)propoxy]-1,2-dihydro-2-oxoquinoline and Related Compounds", Chem. Pharm. Bull, vol. 31, No. 4, pp. 1151-1157, 1983.
English-language abstract of JP A 56-49378.

* cited by examiner

*Primary Examiner* — D M Seaman
(74) *Attorney, Agent, or Firm* — J.A. Lindeman & Co., PLLC

(57) ABSTRACT

The invention relates to improvements of the physiochemical and/or the pharmaceutical properties of cilostazol. Disclosed herein are several new compositions and cocrystals of cilostazol, including: a 1:1 cilostazol gentisic acid cocrystal, a 1:1:1 cilostazol gentisic acid $H_2O$ cocrystal, a 1:1 cilostazol 4-hydroxybenzoic acid cocrystal, and a 1:1 cilostazol 2,4-dihydroxybenzoic acid cocrystal. The therapeutic methods and uses of these cilostazol cocrystals are described as well as therapeutic compositions containing them.

12 Claims, 33 Drawing Sheets

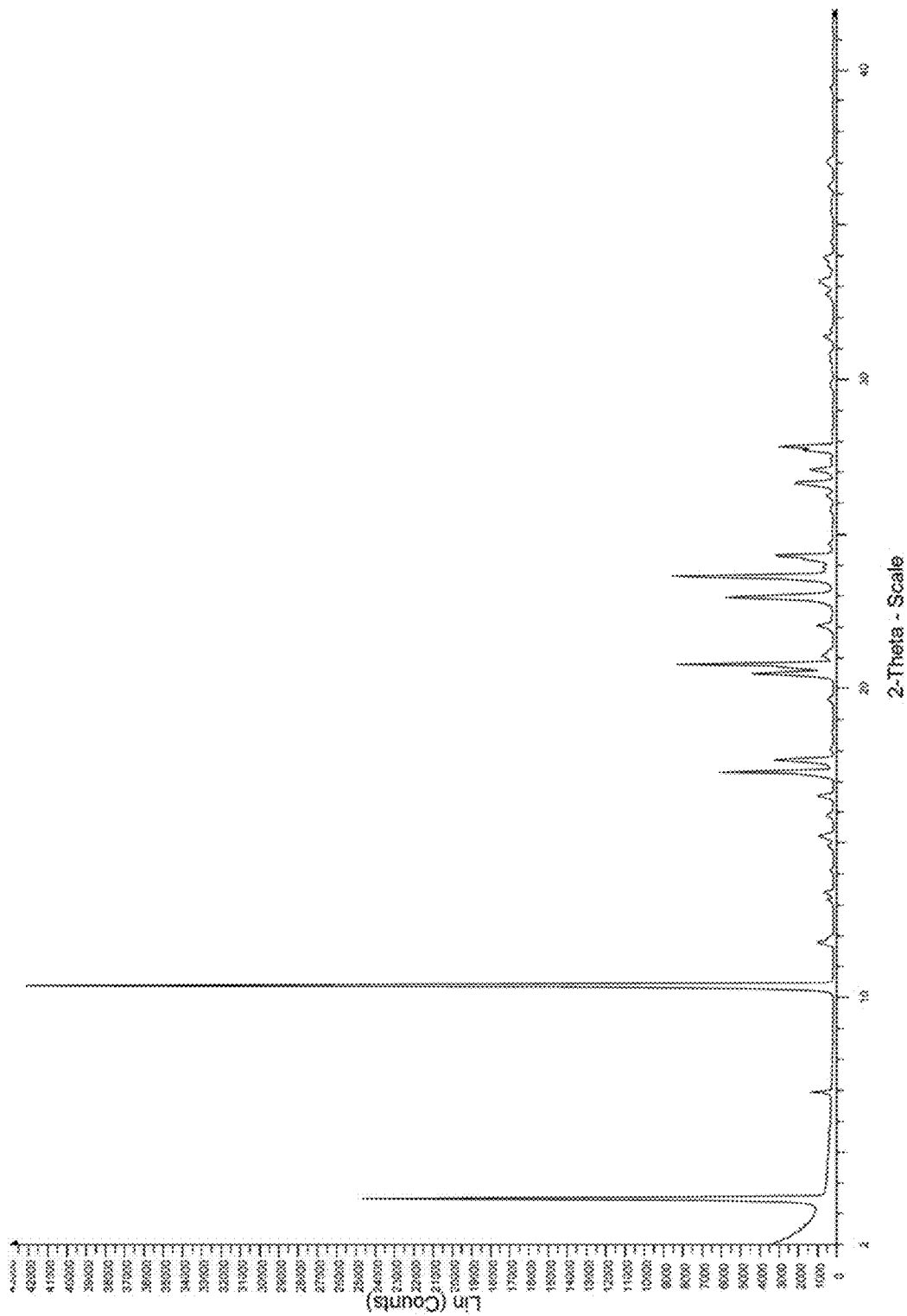
Fig. 1: XRPD Pattern for 1:1 Cilostazol Gentisic Acid Cocrystal

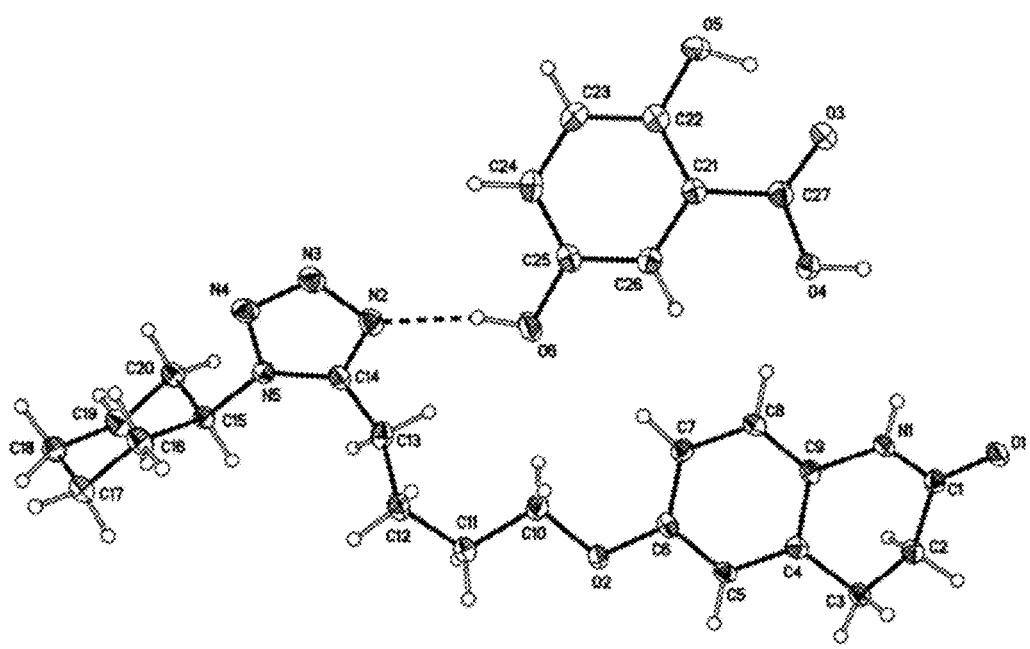
Fig. 2: ORTEP drawing of 1:1 Cilostazol Gentisic Acid Cocrystal

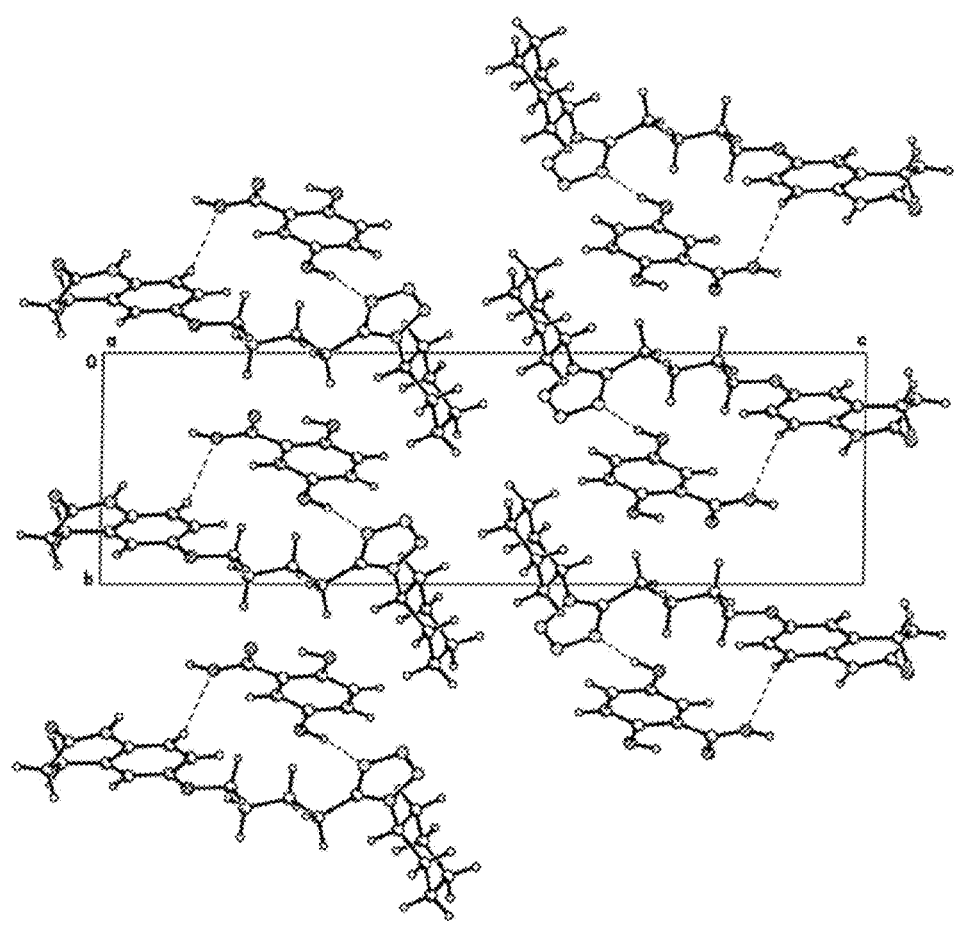
Fig. 3: Packing diagram of 1:1 Cilostazol Gentisic Acid Cocrystal

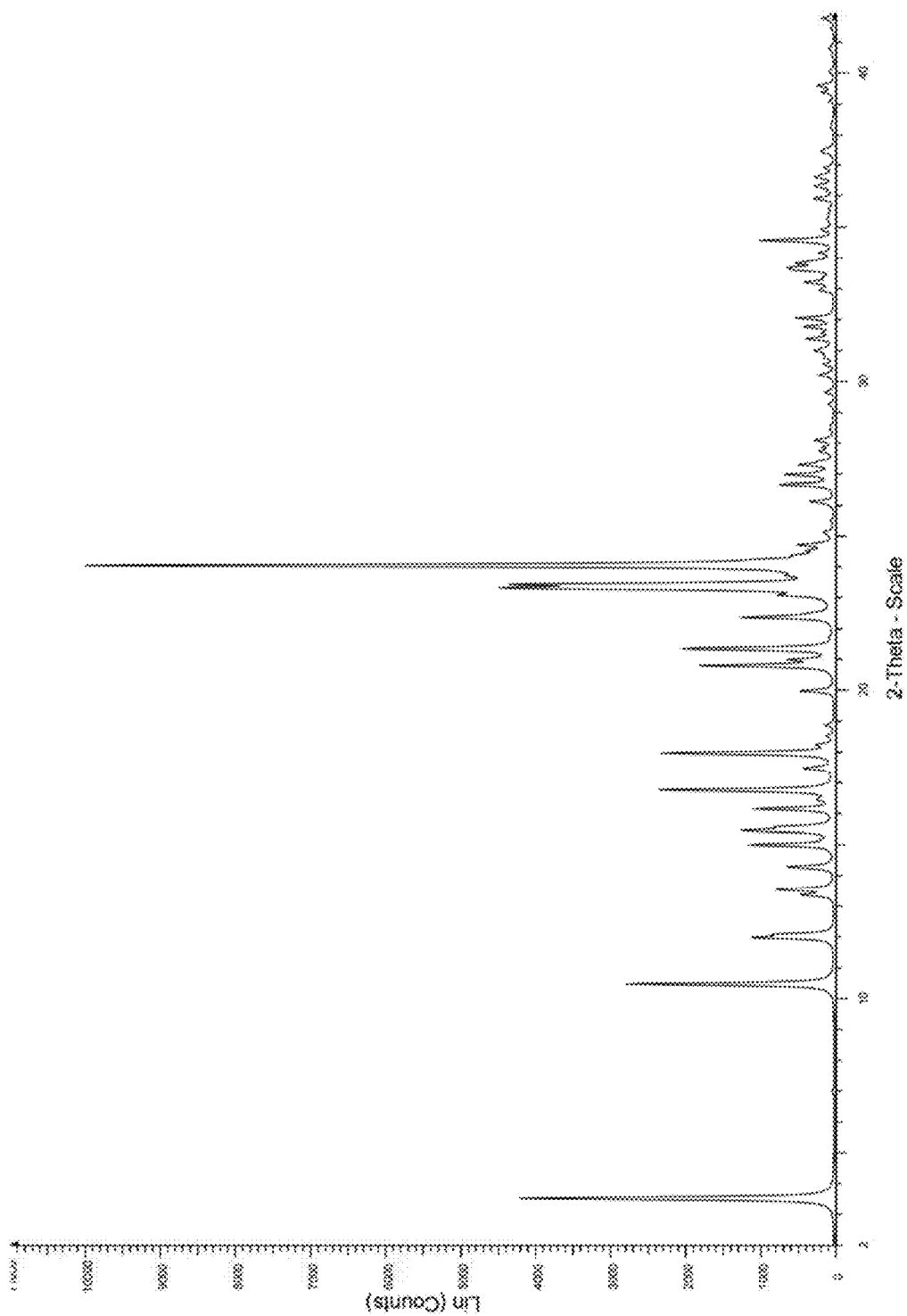
Fig. 4: Calculated XRPD Pattern for 1:1 Cilostazol Gentisic Acid Cocrystal

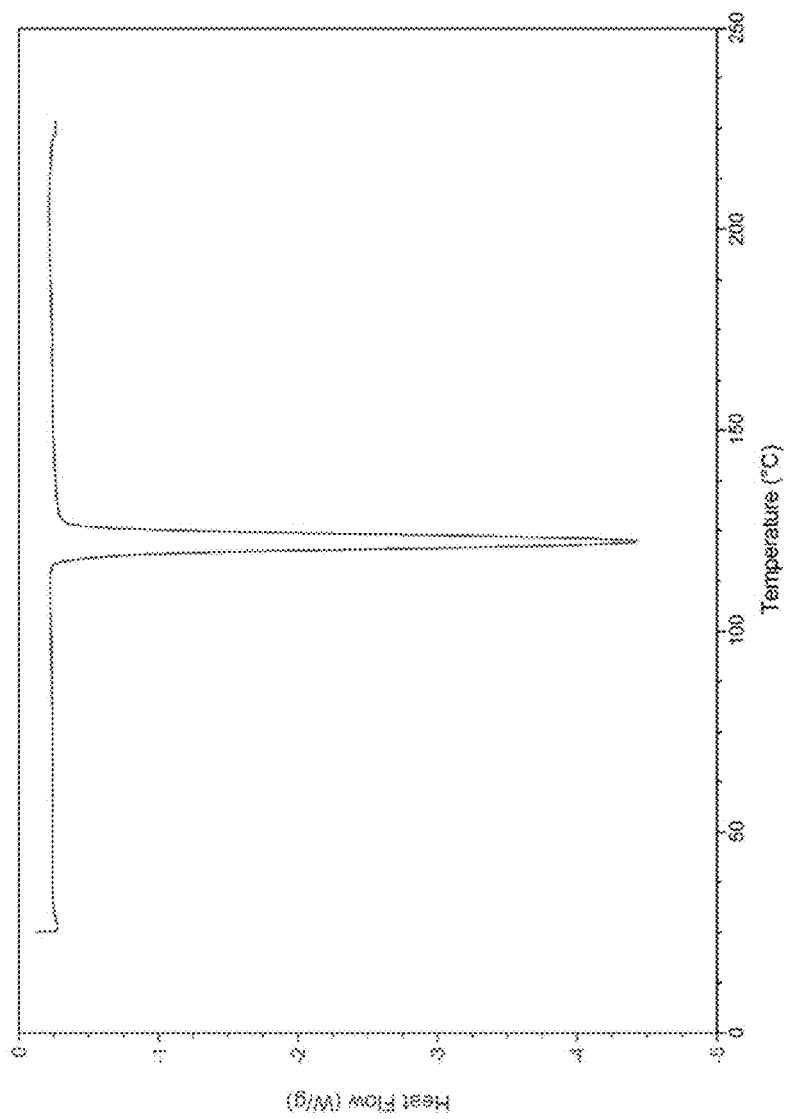

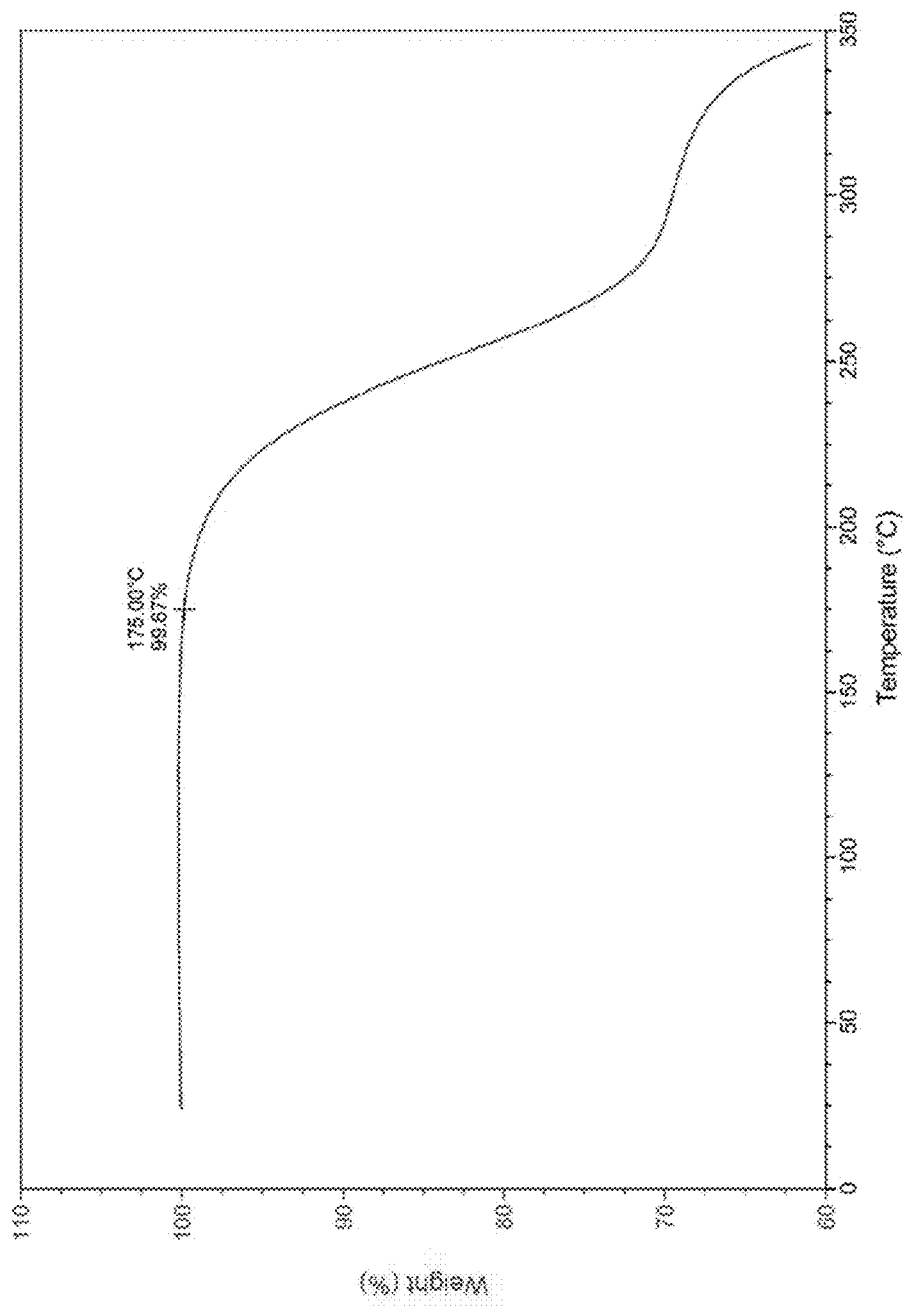
Fig. 6: TGA Trace of a 1:1 Cilostazol Gentisic Acid Cocrystal

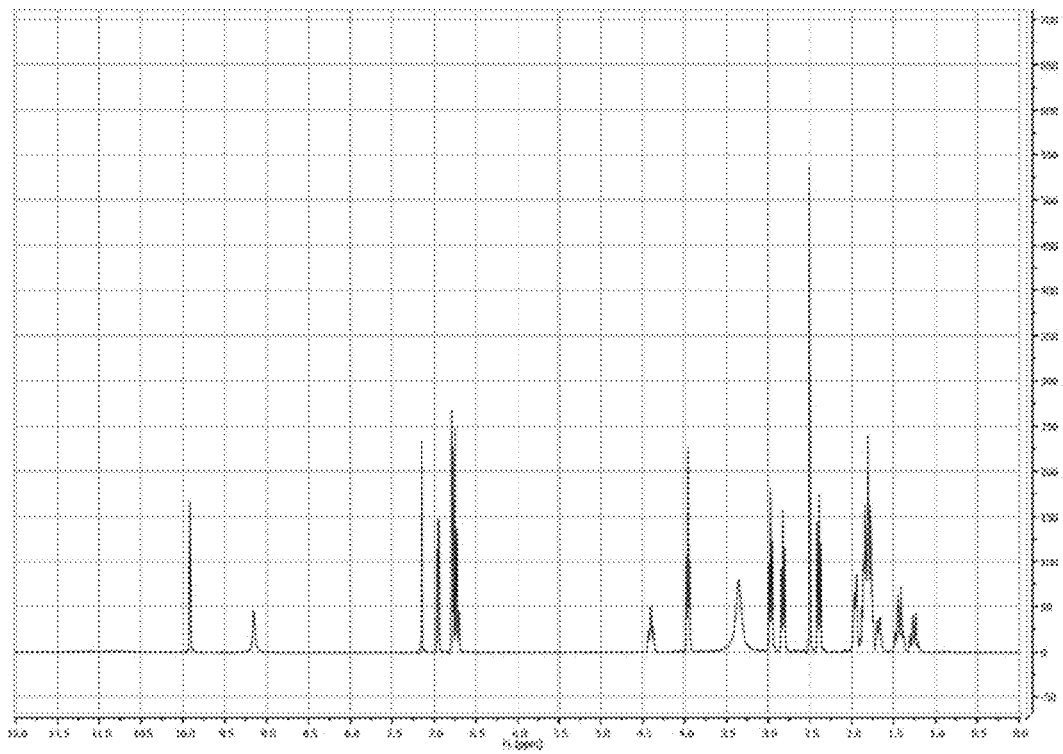
Fig. 7: ¹H NMR Spectrum of a 1:1 Cilostazol Gentisic Acid Cocrystal

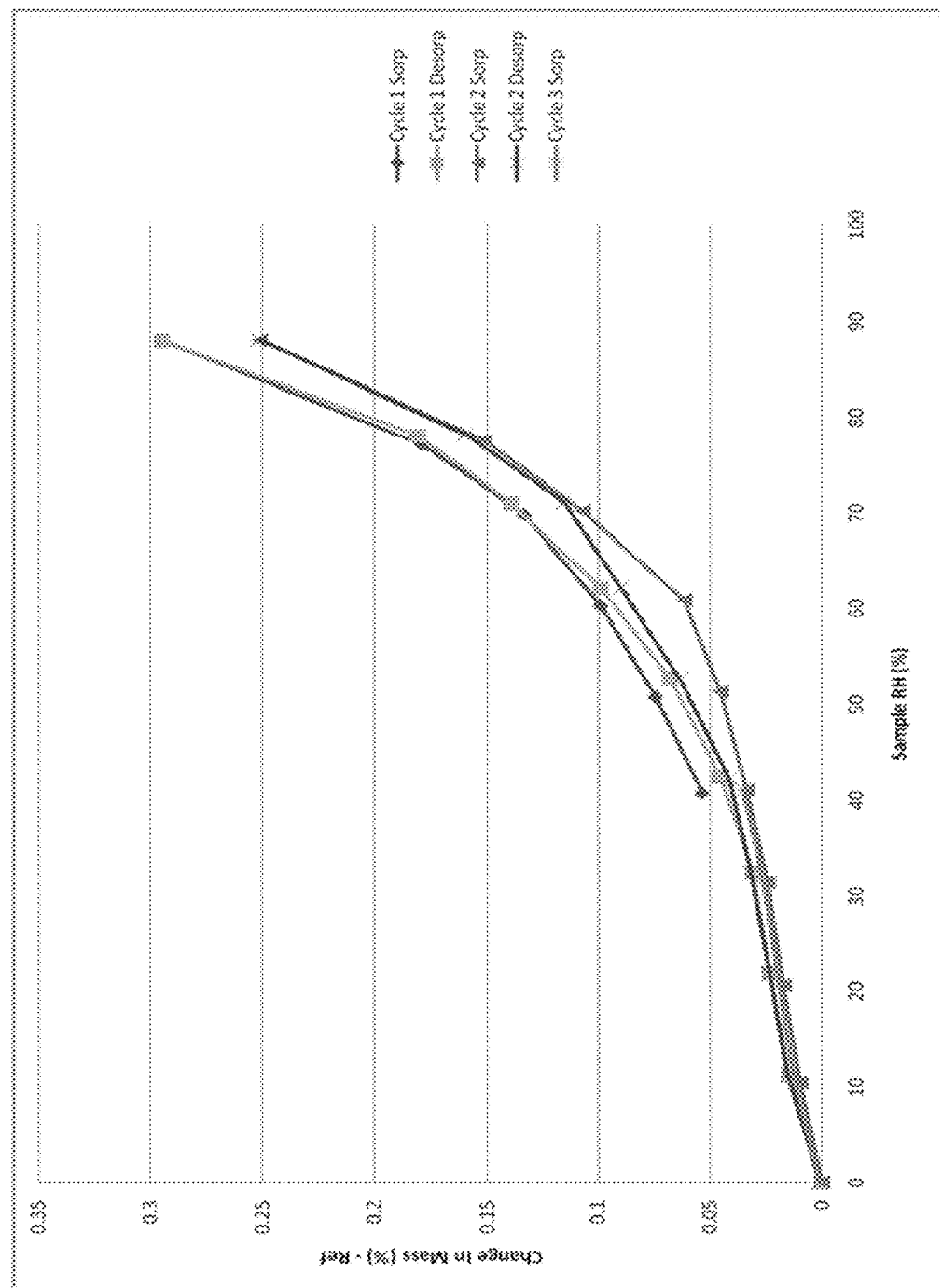

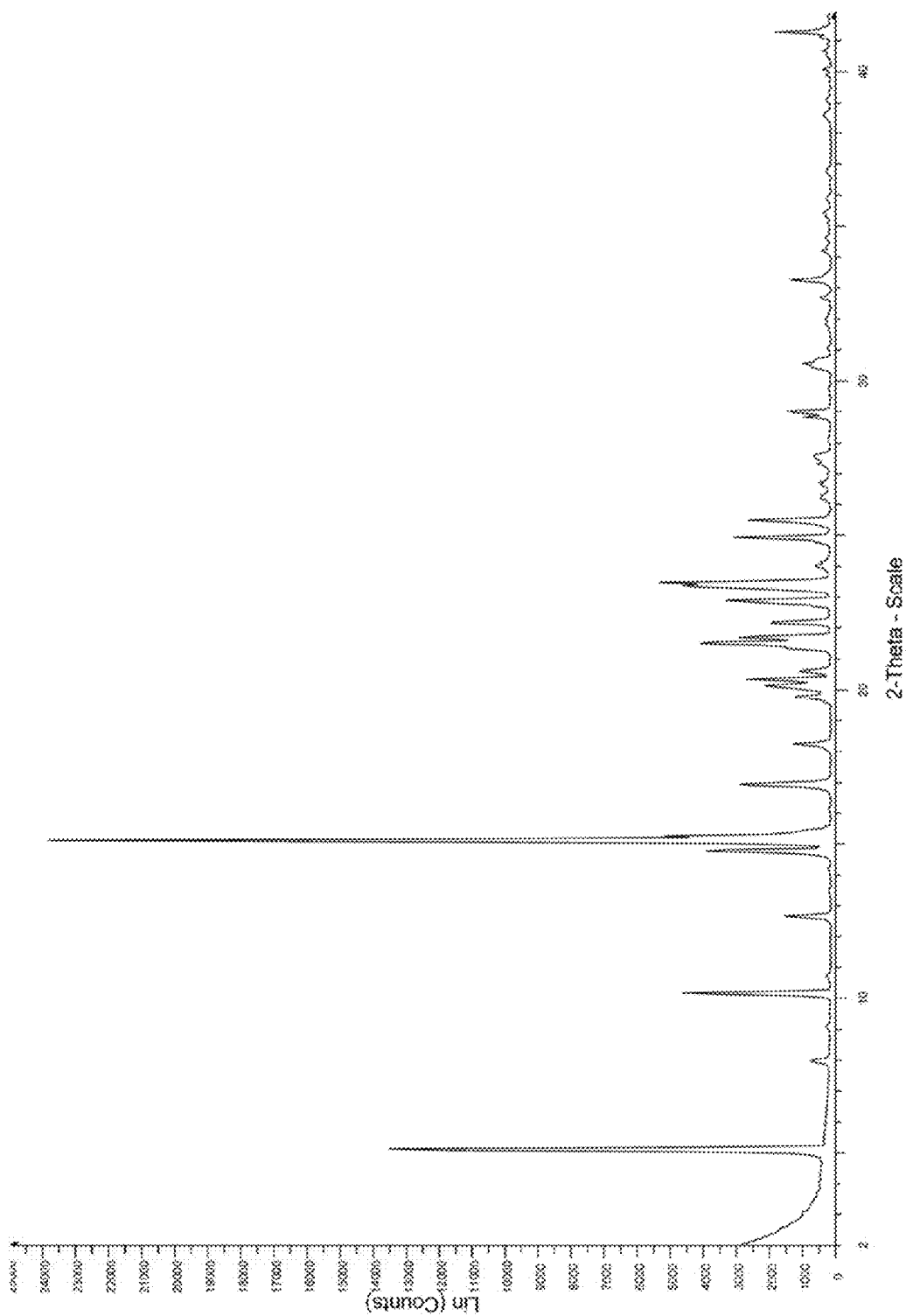
Fig. 9: XRPD Pattern for 1:1:1 Cilostazol Gentisic Acid H₂O Cocrystal

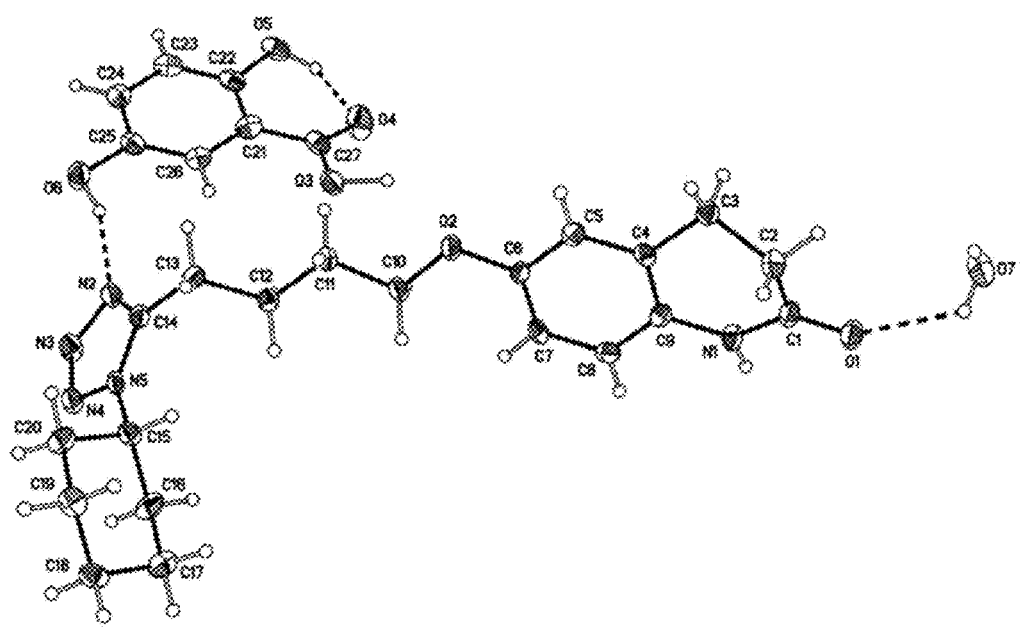
Fig. 10: ORTEP drawing of 1:1:1 Cilostazol Gentisic Acid H₂O Cocrystal

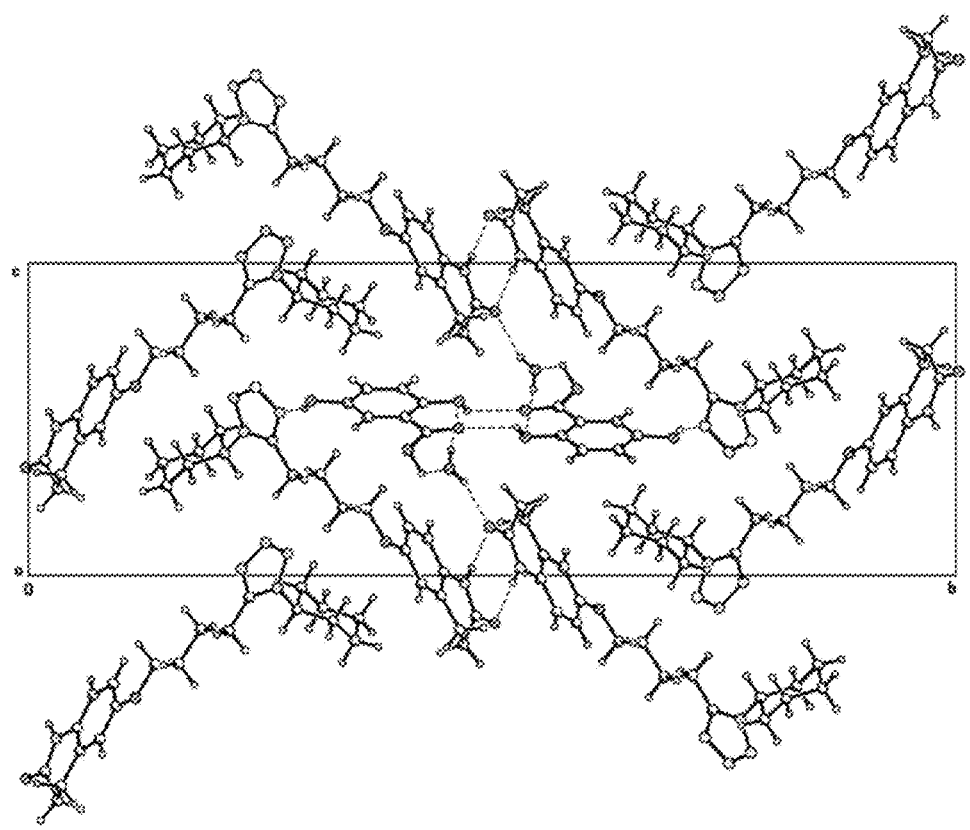
Fig. 11: Packing diagram of 1:1:1 Cilostazol Gentisic Acid $H_2O$ Cocrystal

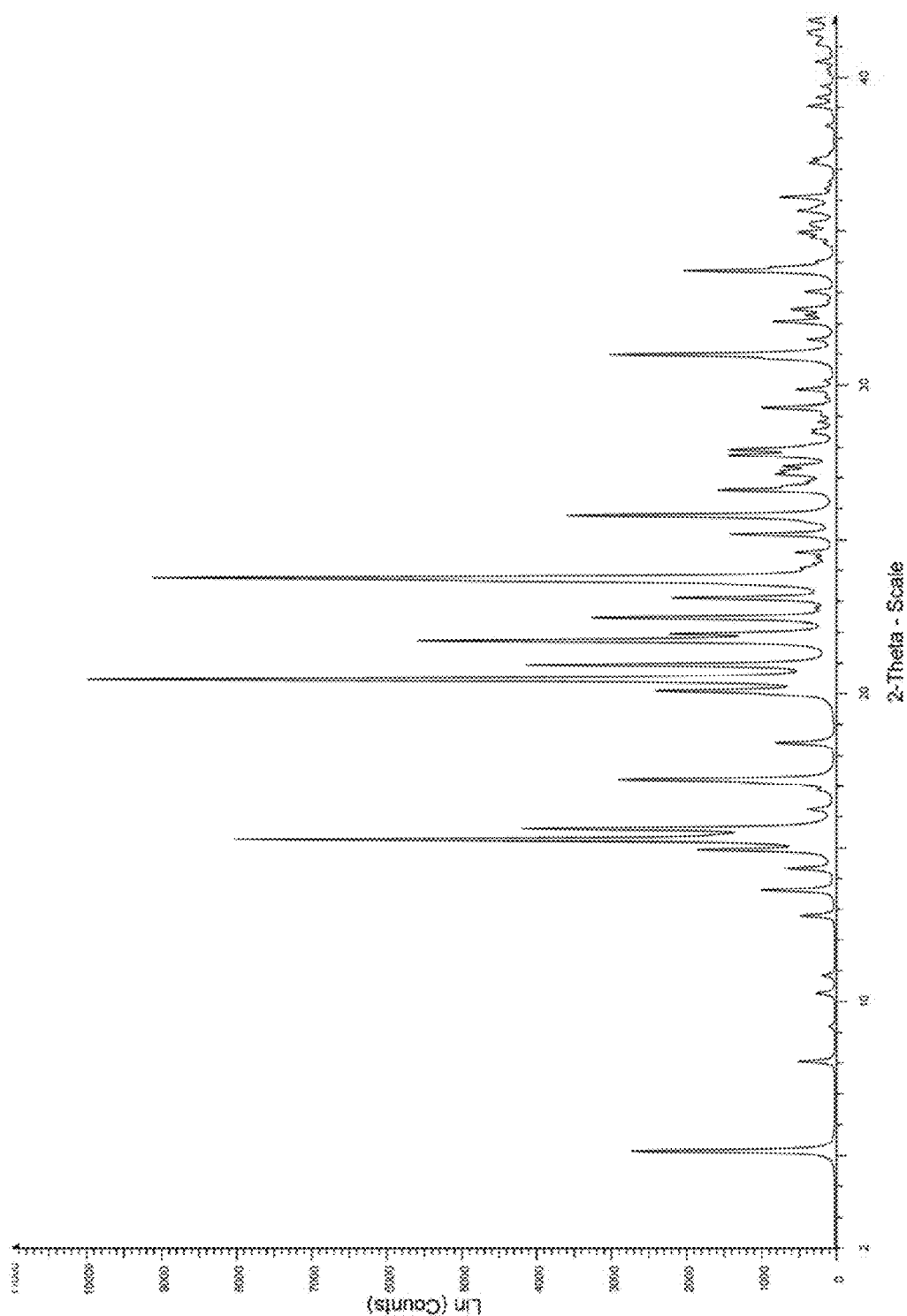
Fig. 12: Calculated XRPD Pattern for 1:1:1 Cilostazol Gentisic Acid H₂O Cocrystal

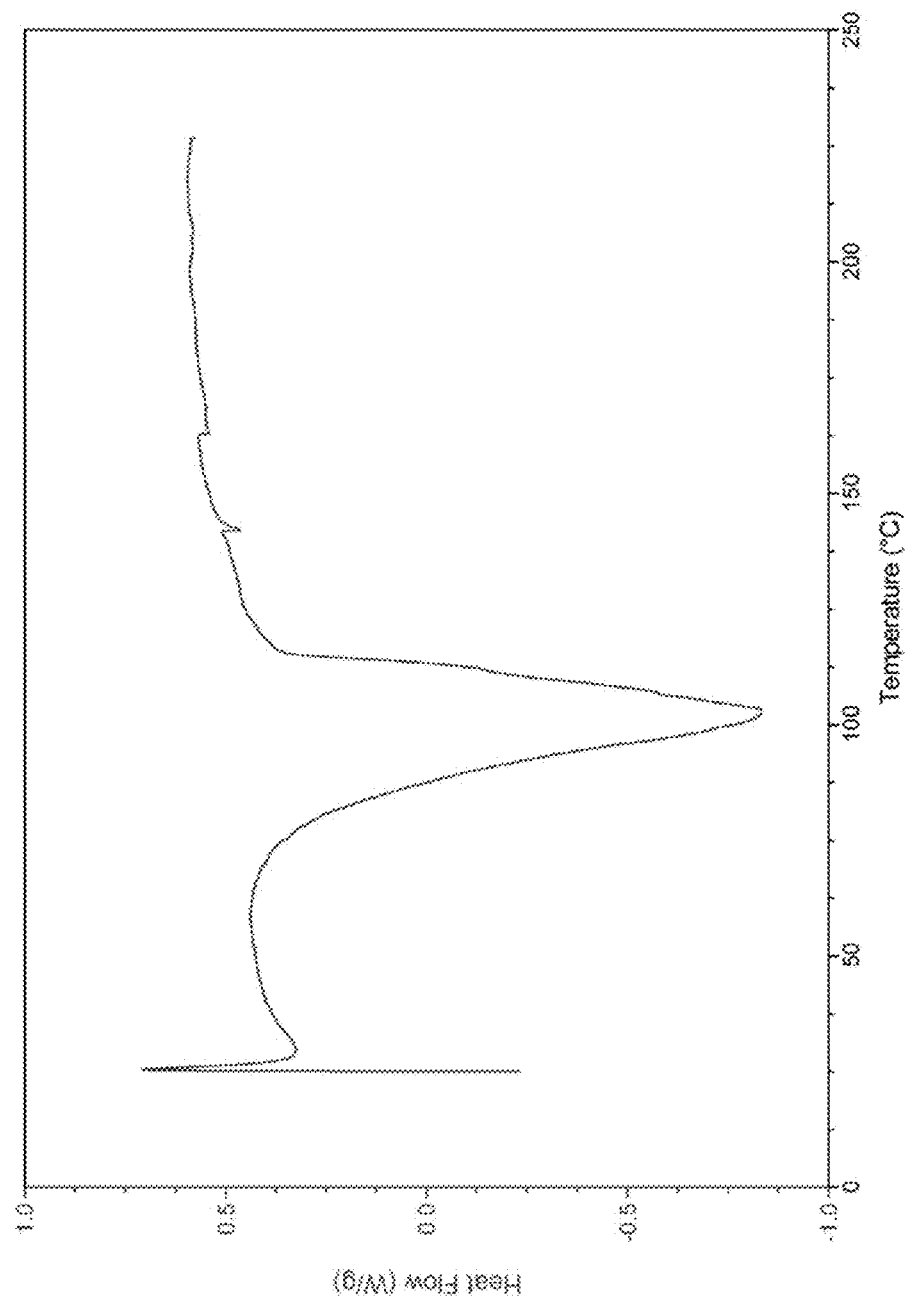

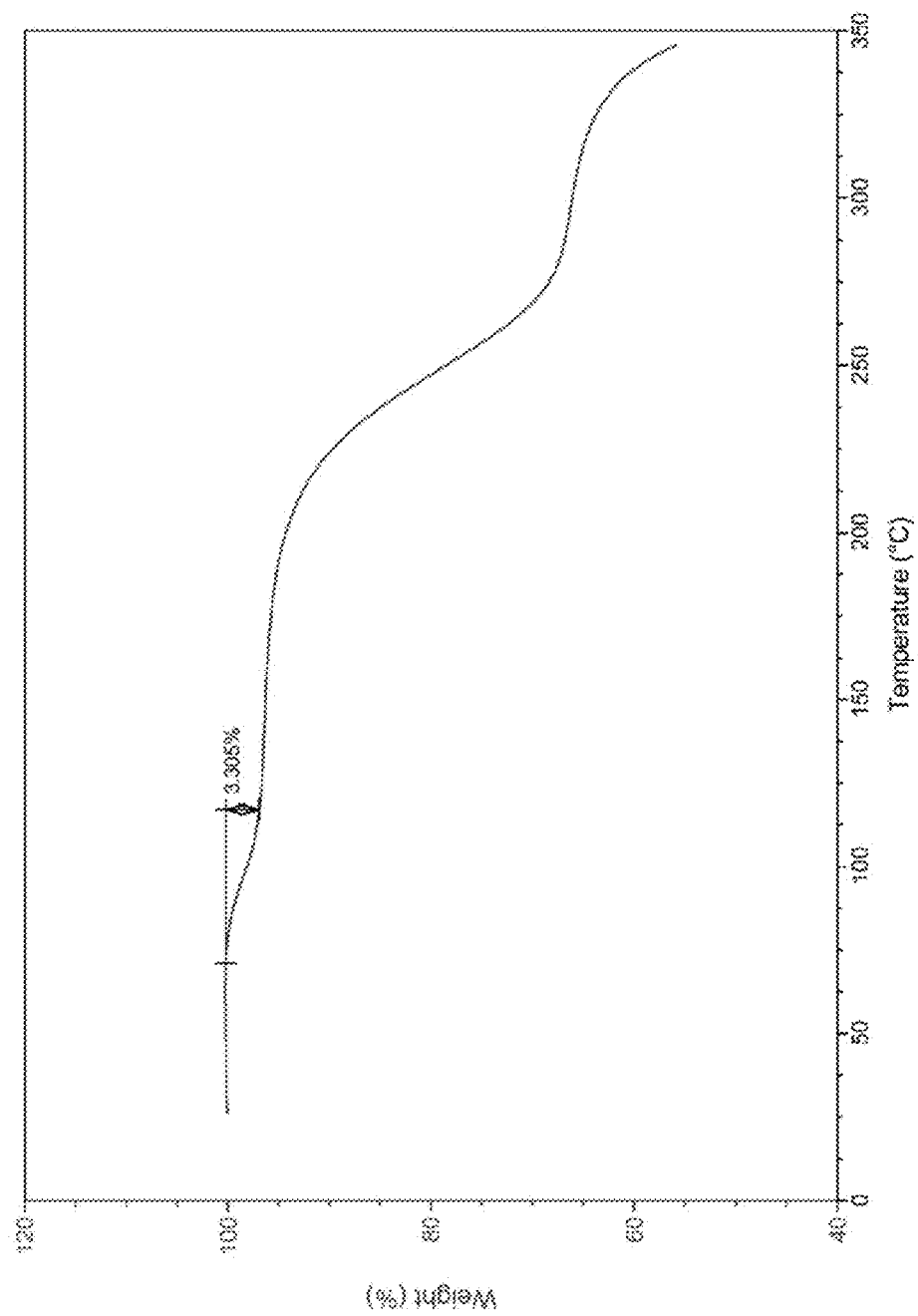

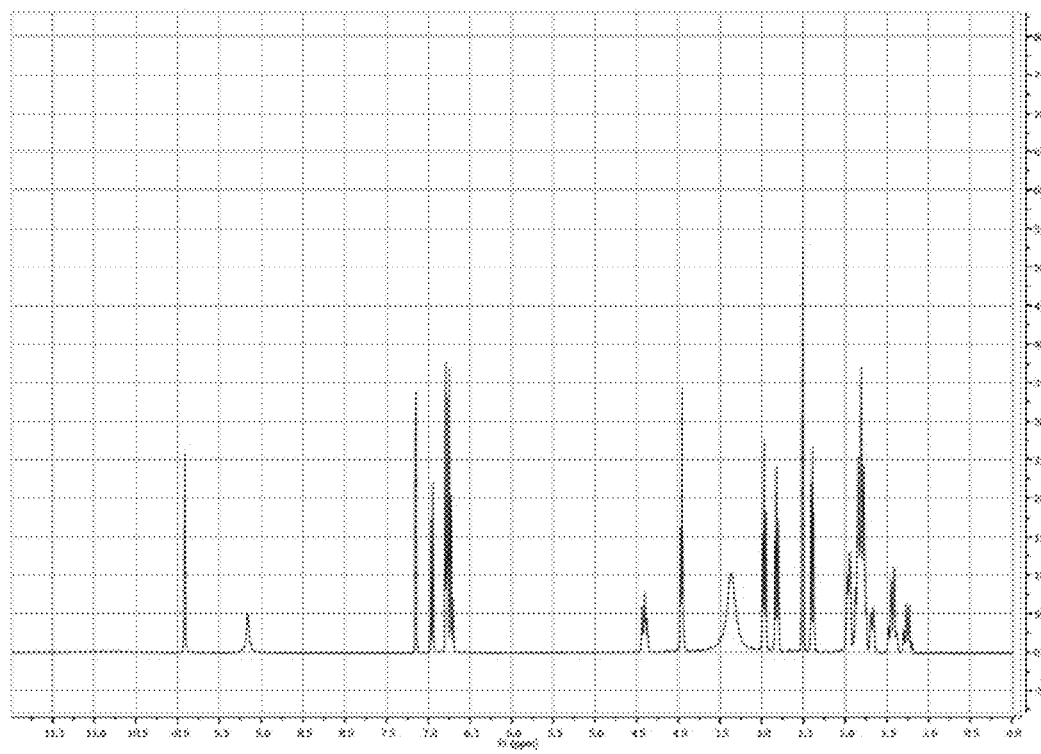
Fig. 15: ¹H NMR Spectrum of a 1:1:1 Cilostazol Gentisic Acid H₂O Cocrystal

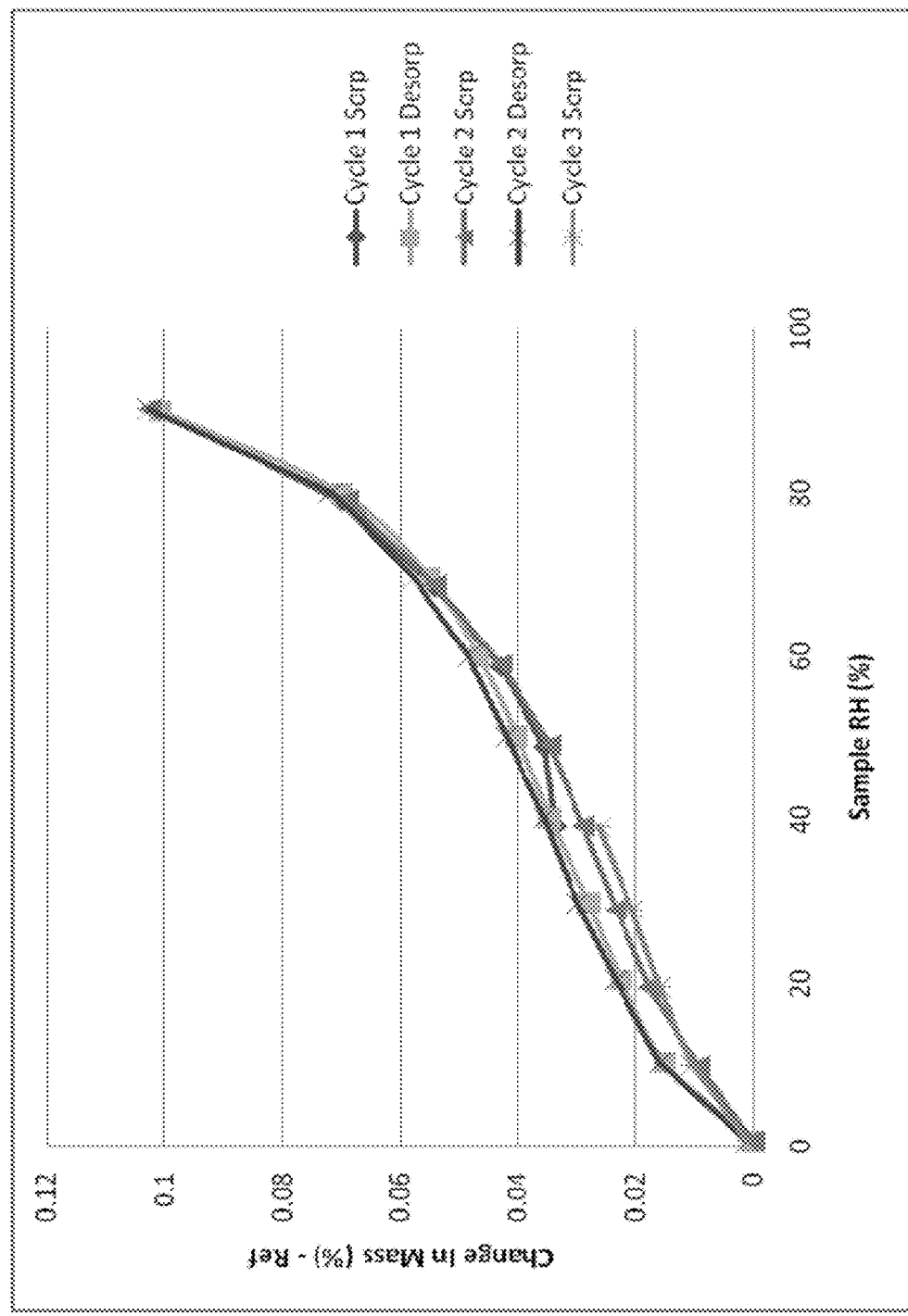
Fig. 16: GVS Isotherm Graphs for the 1:1:1 Cilostazol Gentisic Acid $H_2O$ Cocrystal

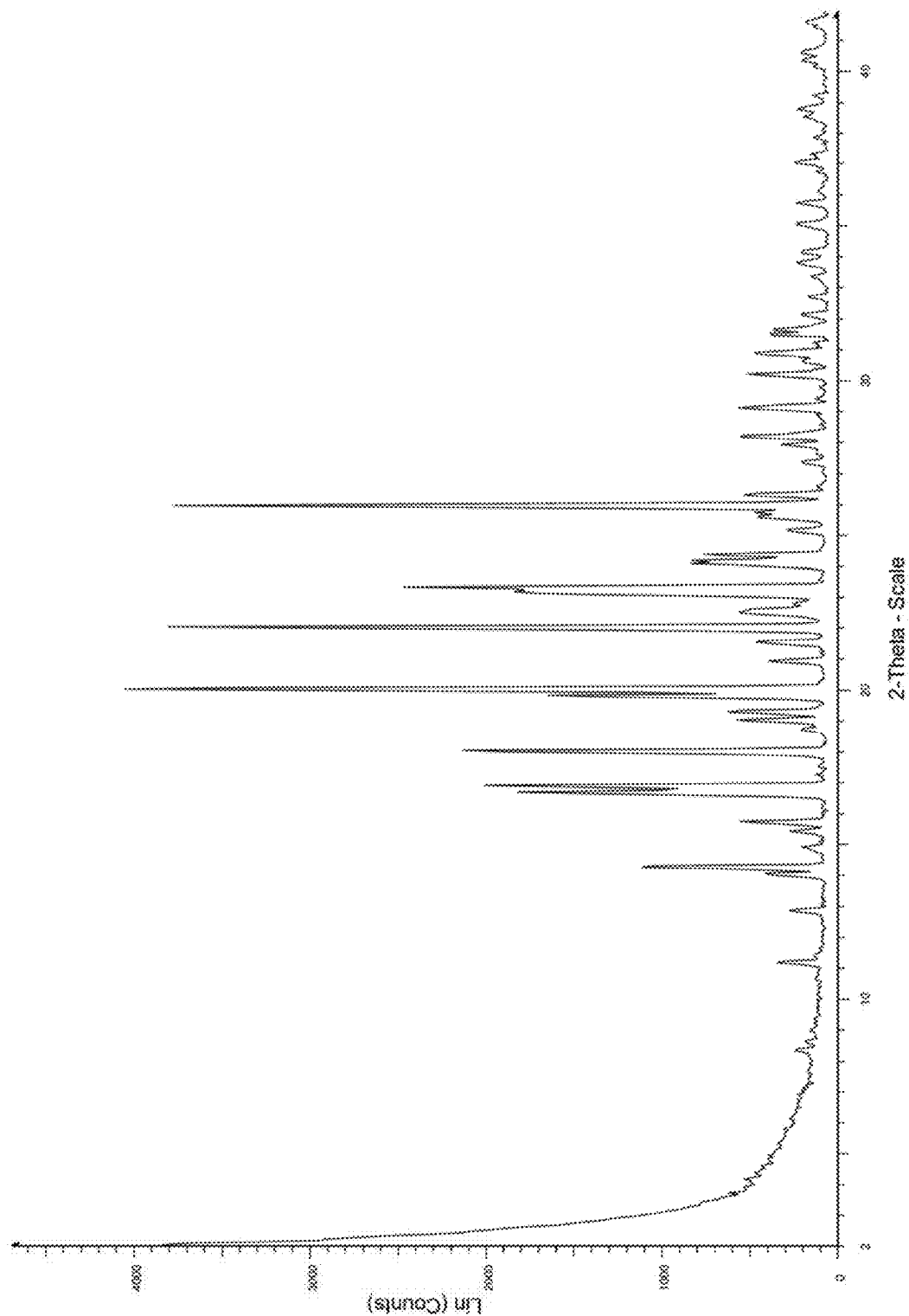
Fig. 17: XRPD Pattern for 1:1 Cilostazol 4-Hydroxybenzoic Acid Cocrystal

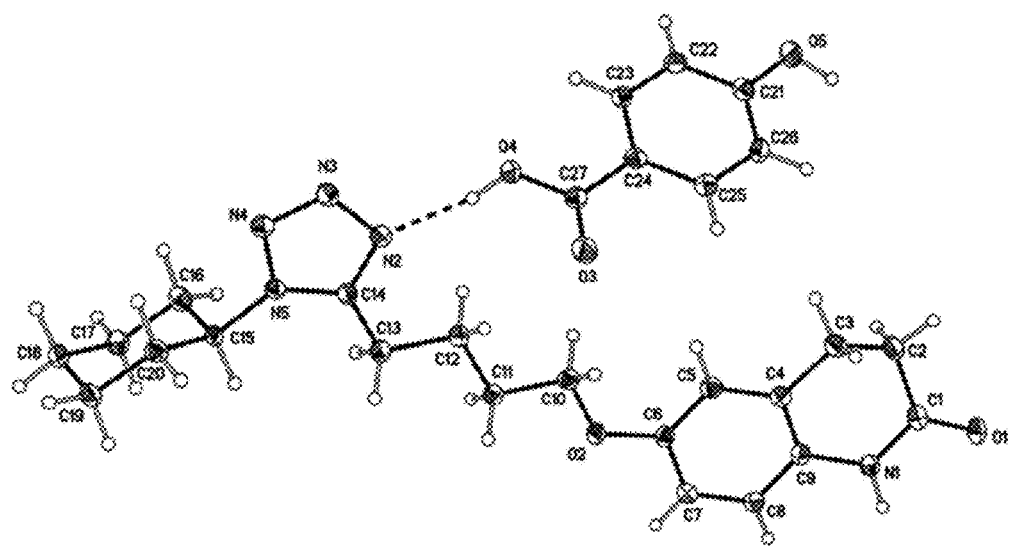
Fig. 18: ORTEP diagram of 1:1 Cilostazol 4-Hydroxybenzoic Acid Cocrystal

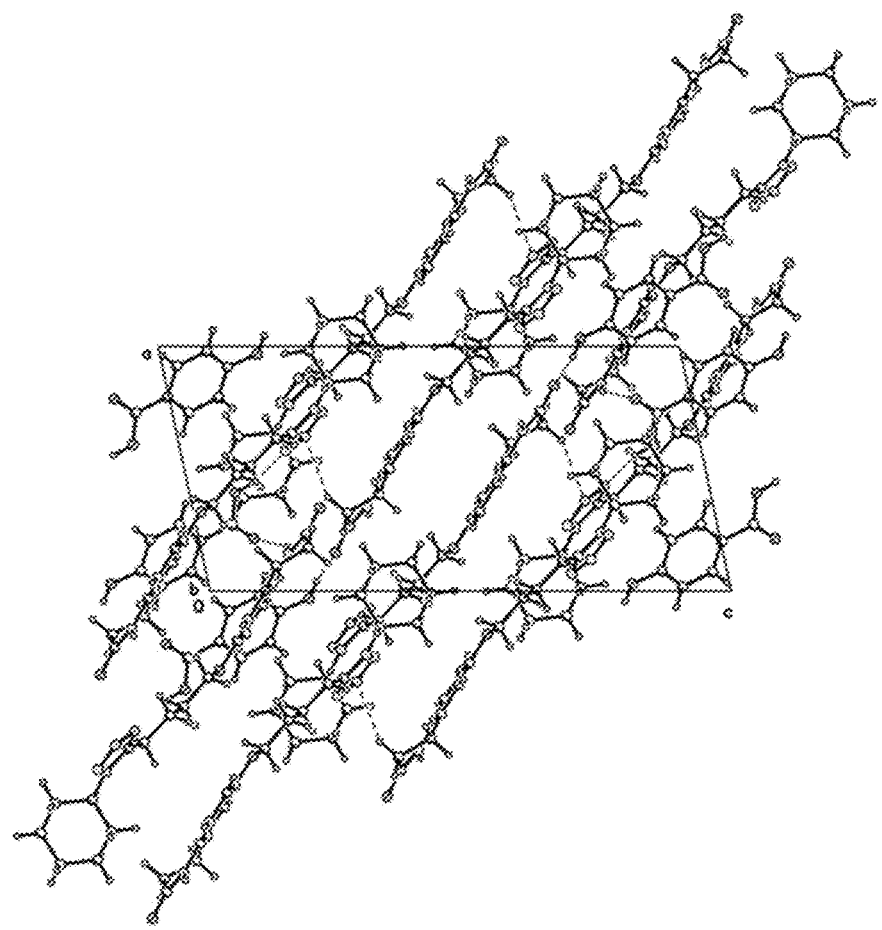
Fig. 19: Packing diagram of 1:1 Cilostazol 4-Hydroxybenzoic Acid Cocrystal

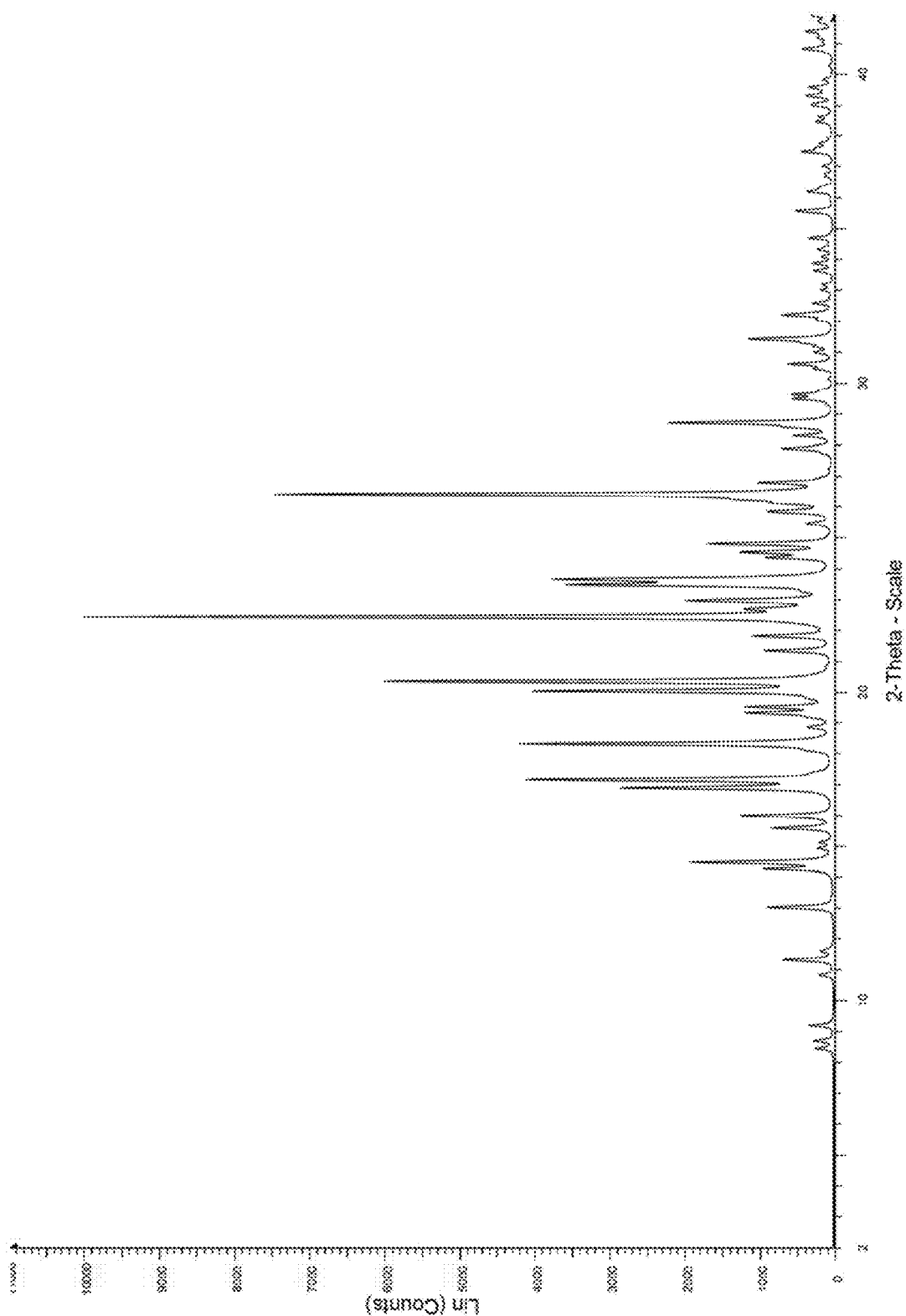
Fig. 20: Calculated XRPD Pattern for 1:1 Cilostazol 4-Hydroxybenzoic Acid Cocrystal

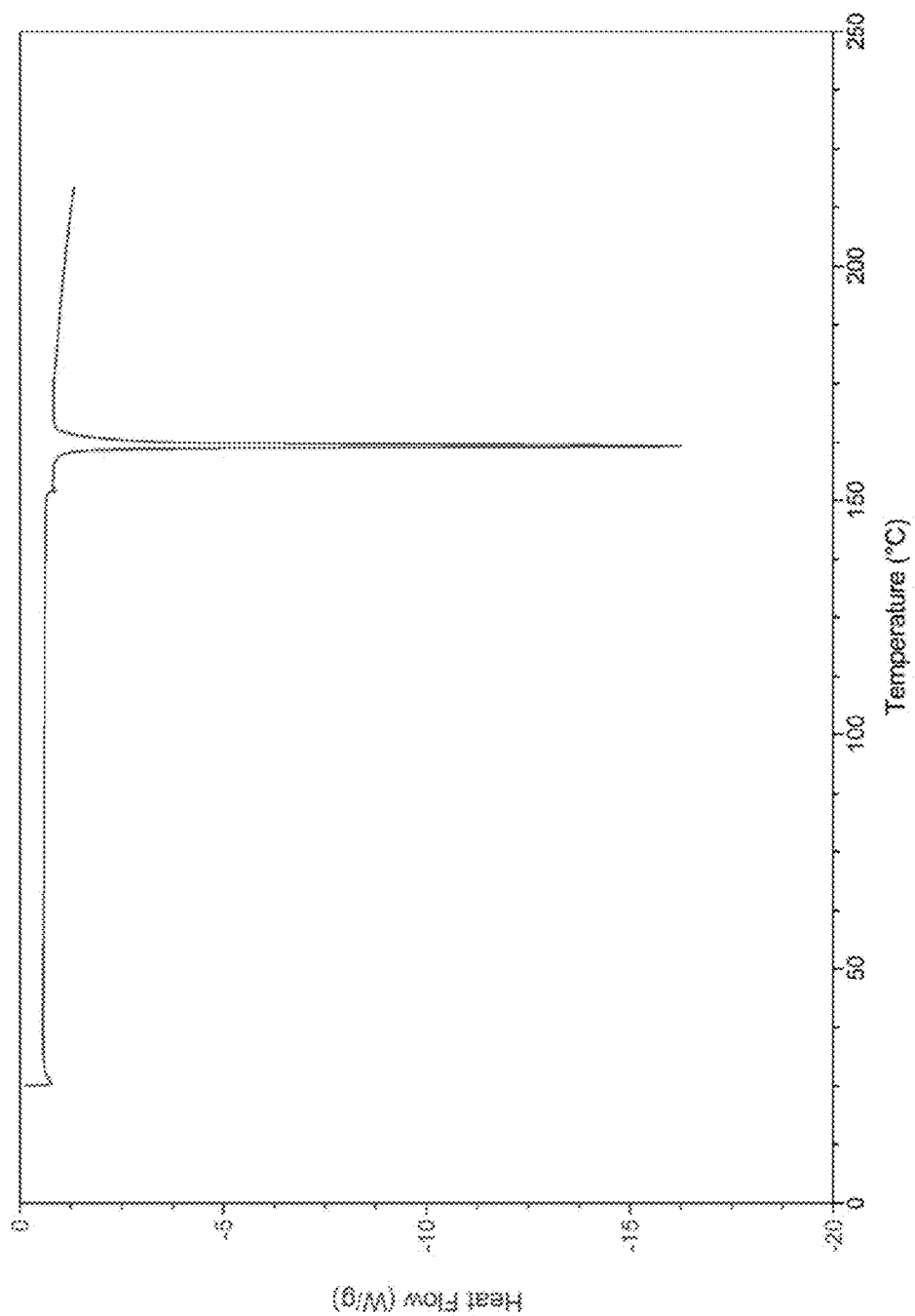
Fig. 21: DSC Trace For a 1:1 Cilostazol 4-Hydroxybenzoic Acid Cocrystal

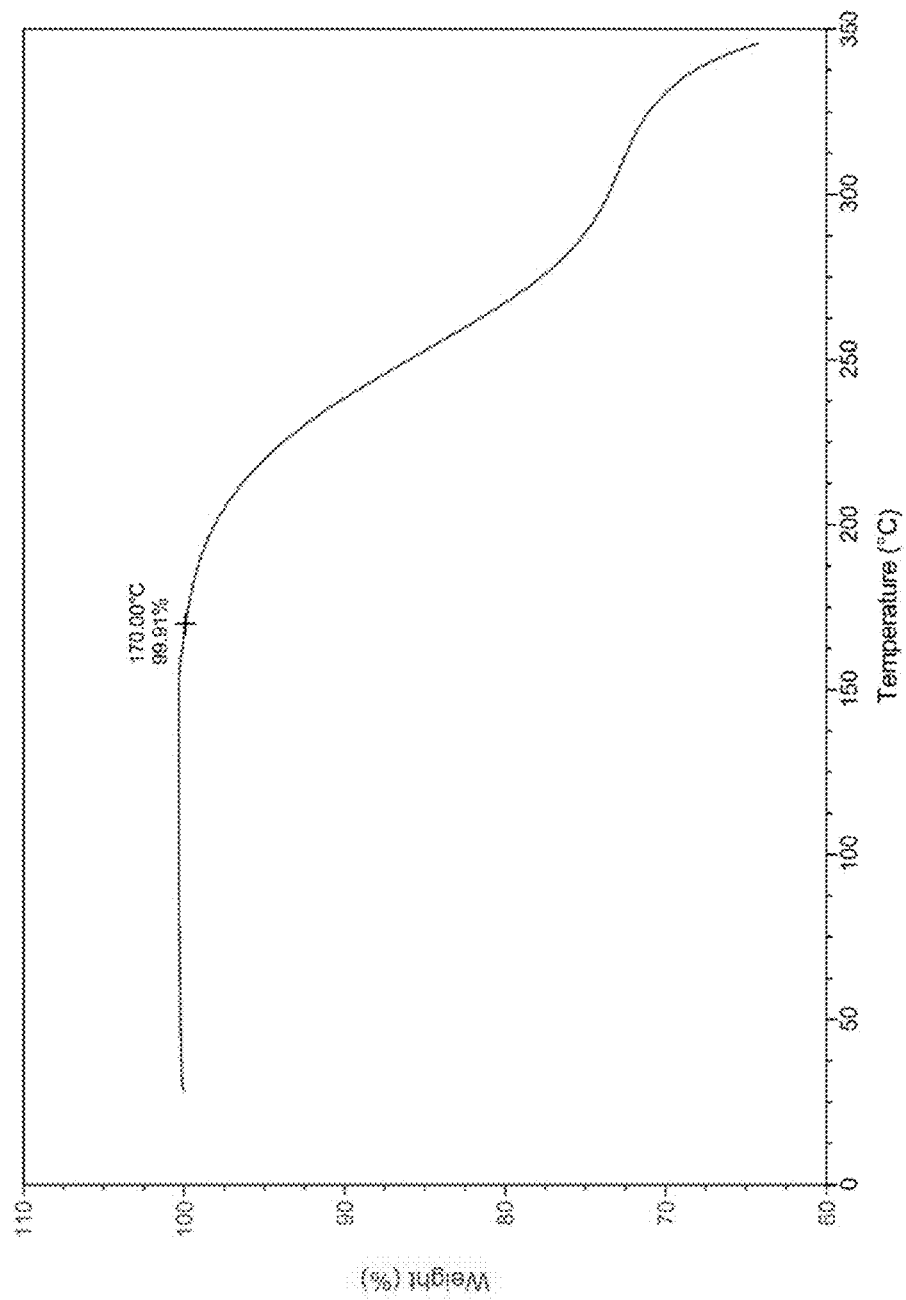
Fig. 22: TGA Trace For a 1:1 Cilostazol 4-Hydroxybenzoic acid Cocrystal

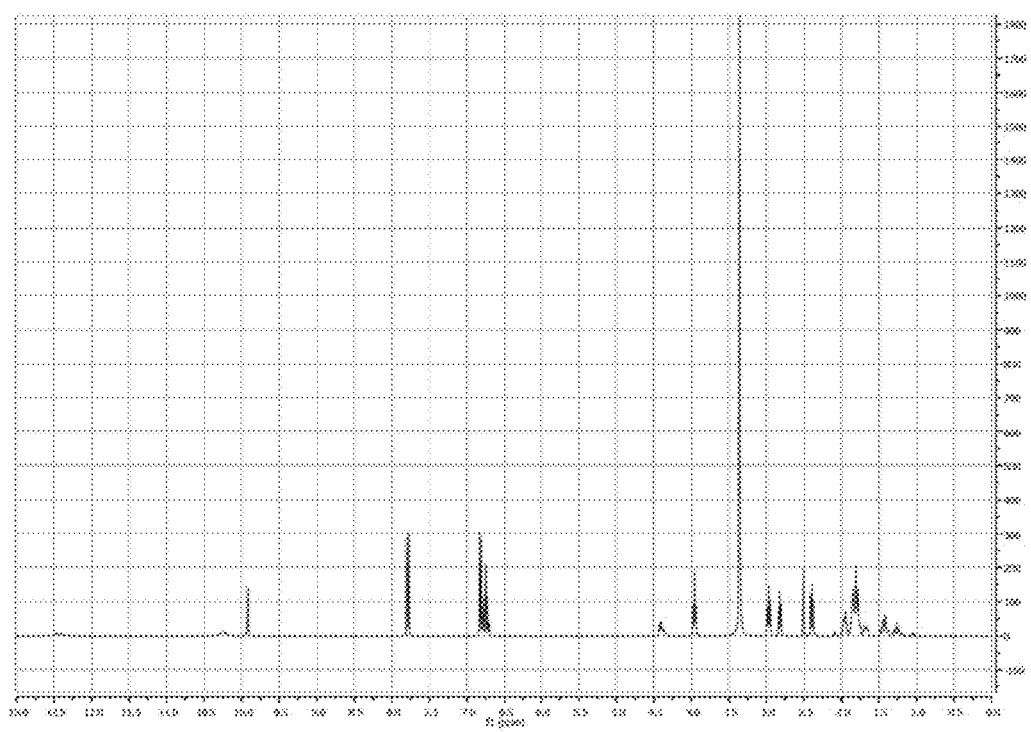
Fig. 23: ¹H NMR Spectrum of a 1:1 Cilostazol 4-Hydroxybenzoic Acid Cocrystal

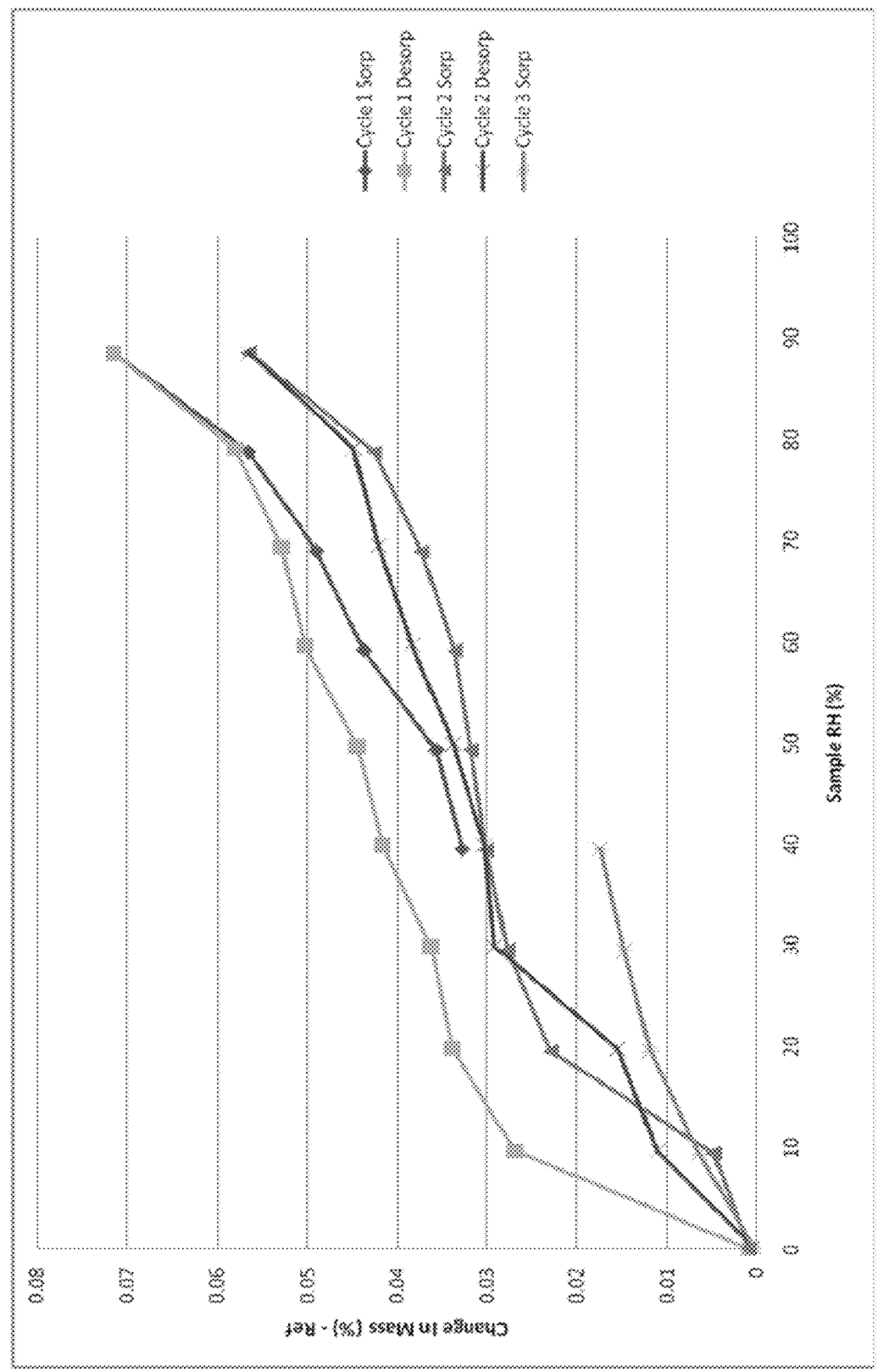
Fig. 24: GVS Isotherm Graphs for the 1:1 Cilostazol 4-Hydroxybenzoic Acid Cocrystal

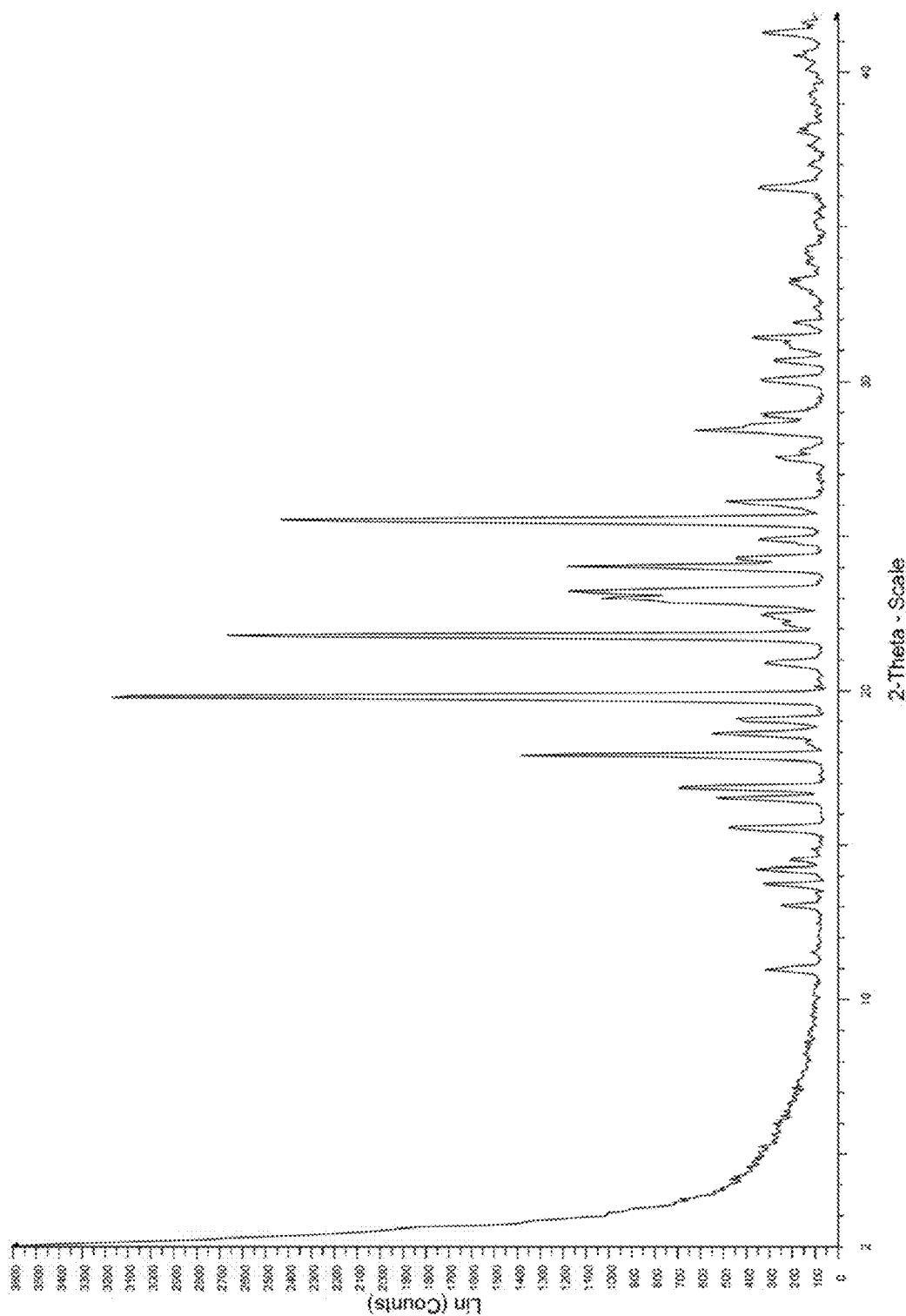

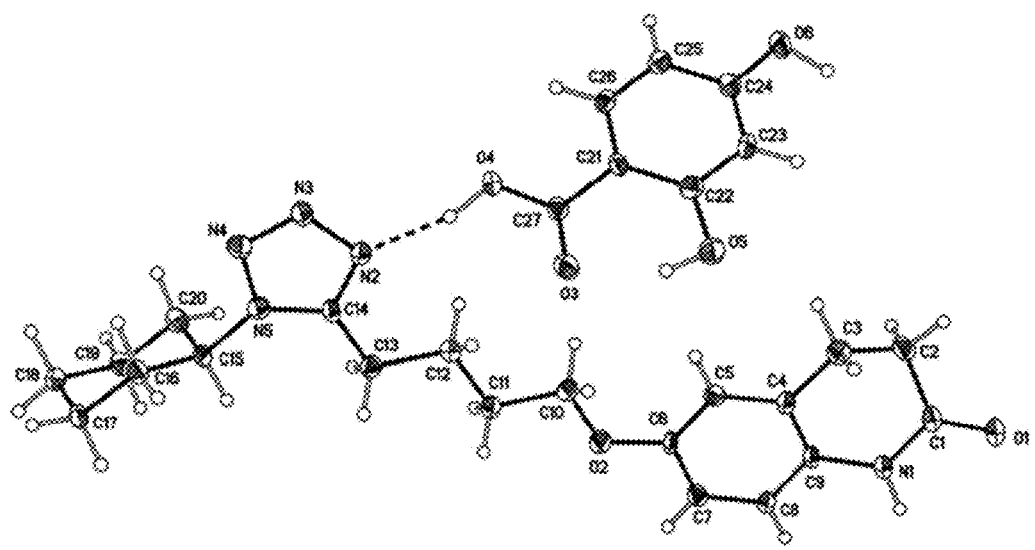
Fig. 26: ORTEP diagram of 1:1 Cilostazol 2,4-Dihydroxybenzoic Acid Cocrystal

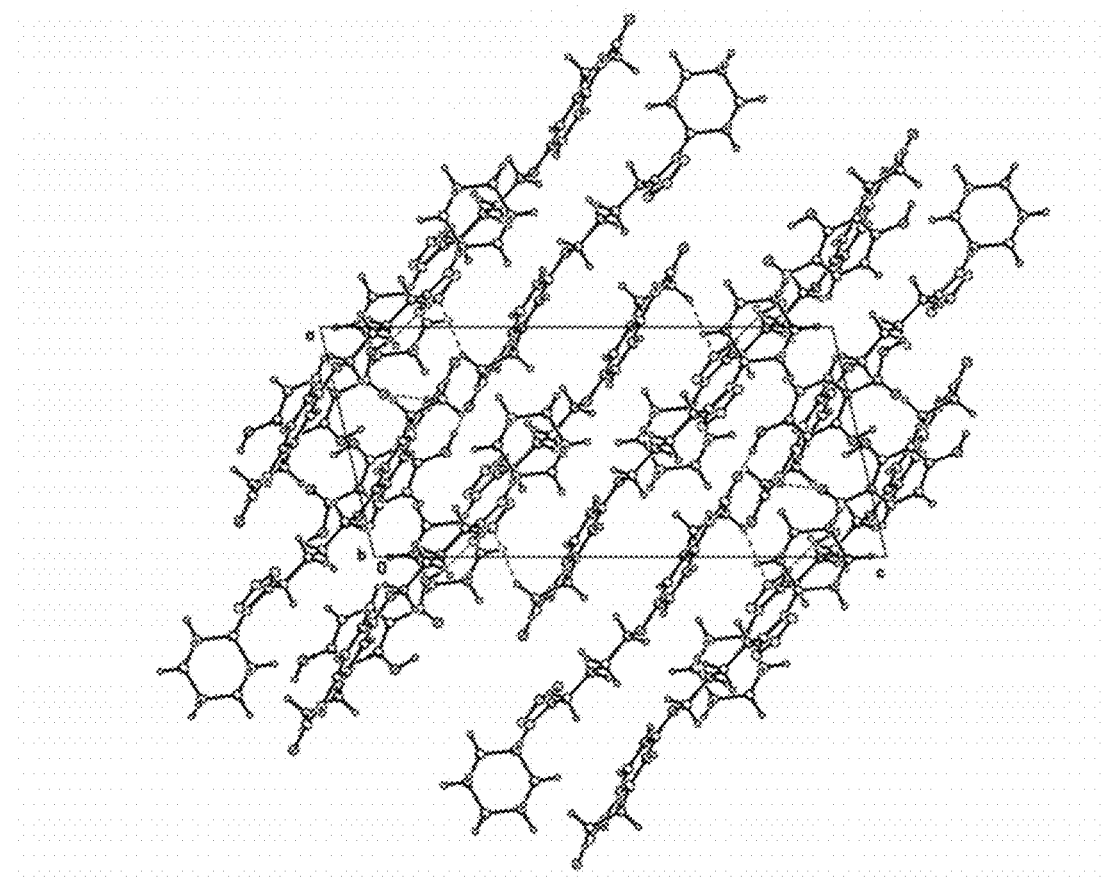
Fig. 27: Packing diagram of 1:1 Cilostazol 2,4-Dihydroxybenzoic Acid Cocrystal

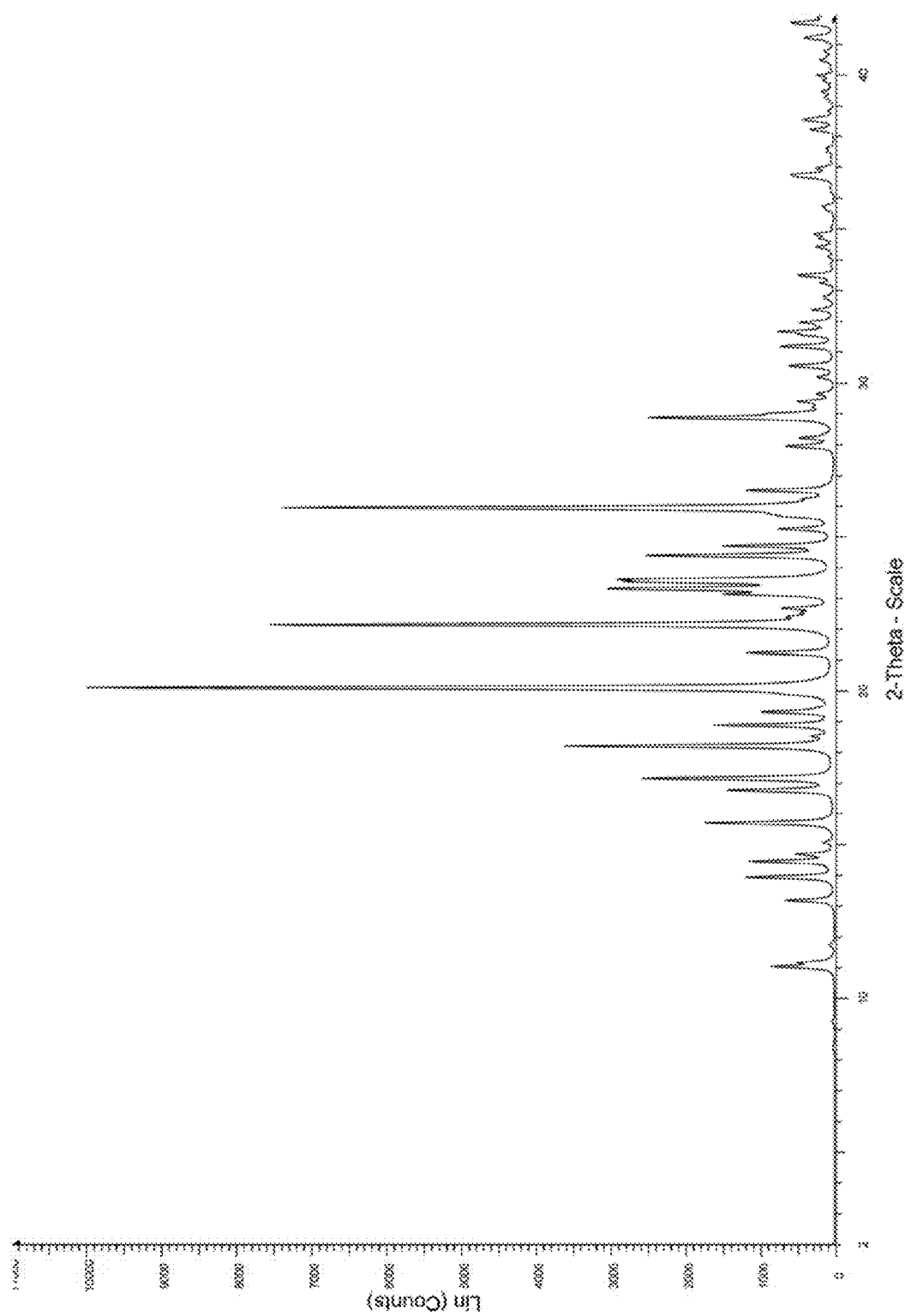

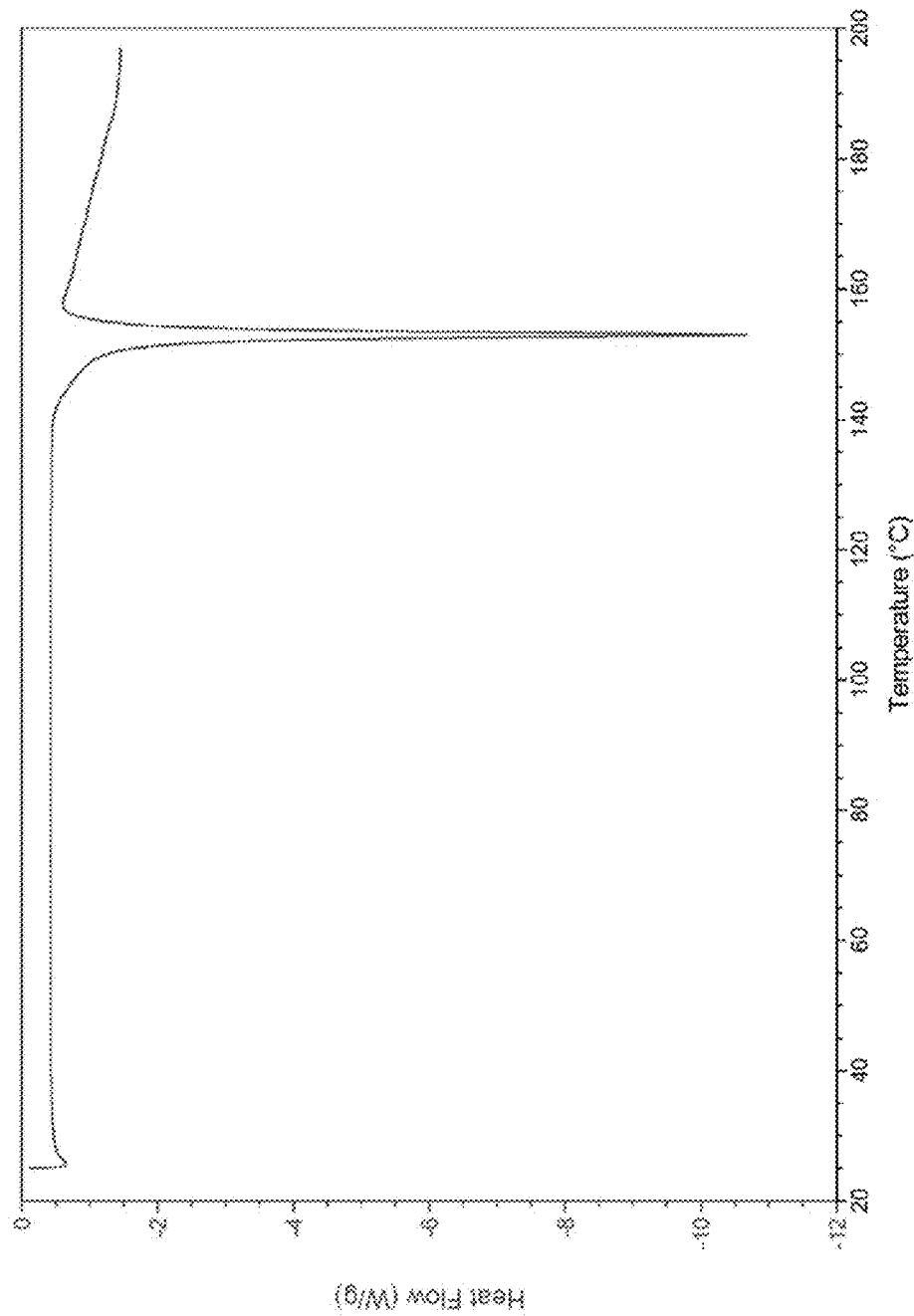
Fig. 29: DSC Trace for a 1:1 Cilostazol 2,4-Dihydroxybenzoic acid Cocrystal

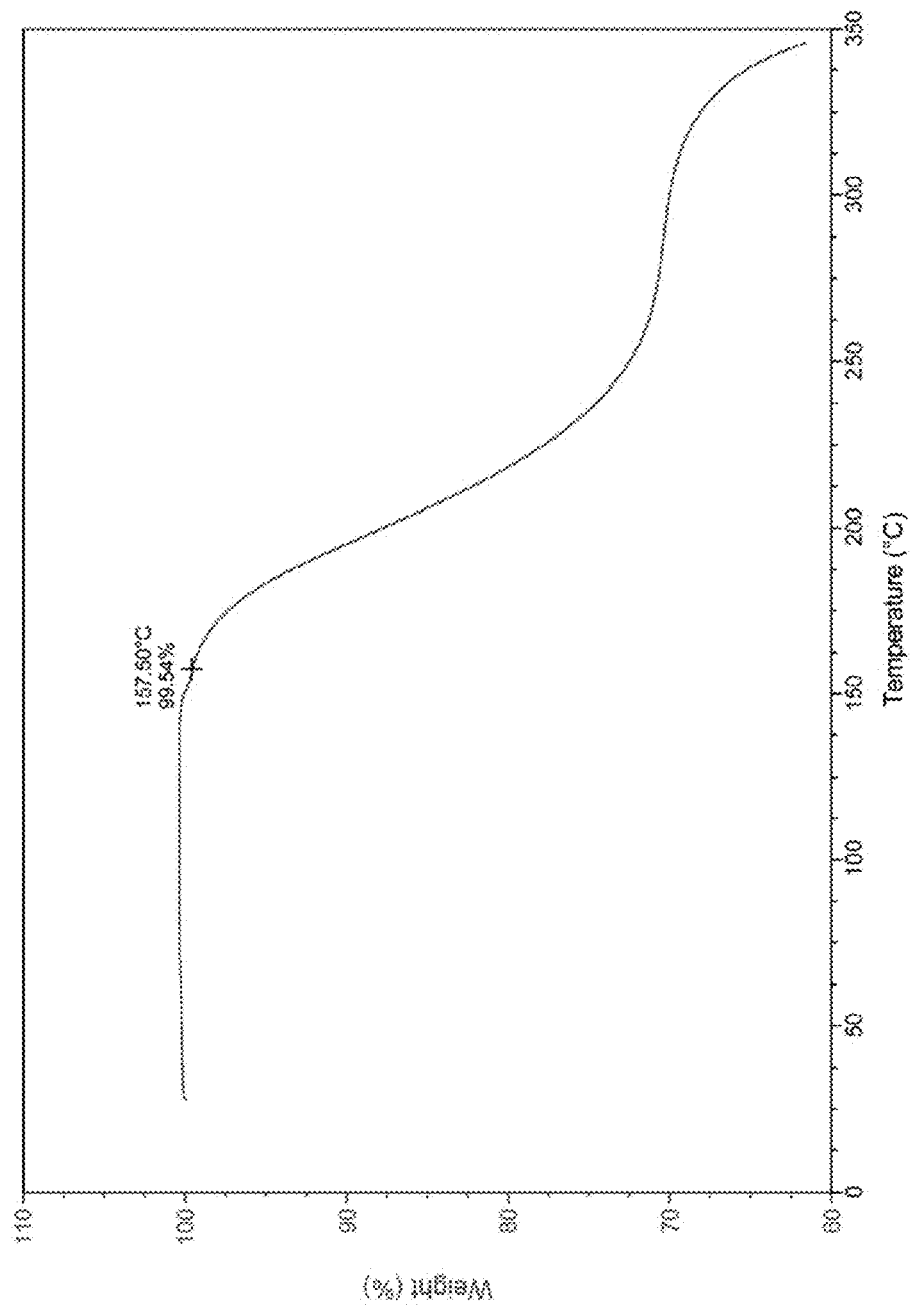
Fig. 30: TGA Traced for a 1:1 Cilostazol 2,4-Dihydroxybenzoic acid Cocrystal

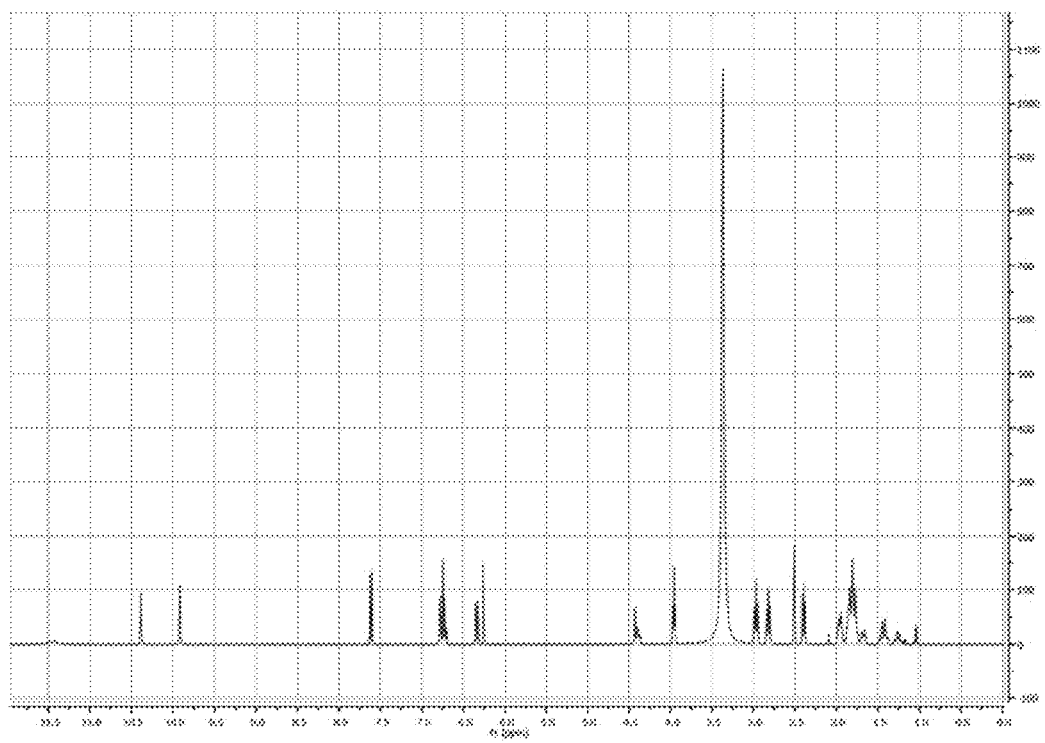
Fig. 31: ¹H NMR Spectrum of a 1:1 Cilostazol 2,4-Dihydroxybenzoic Acid Cocrystal

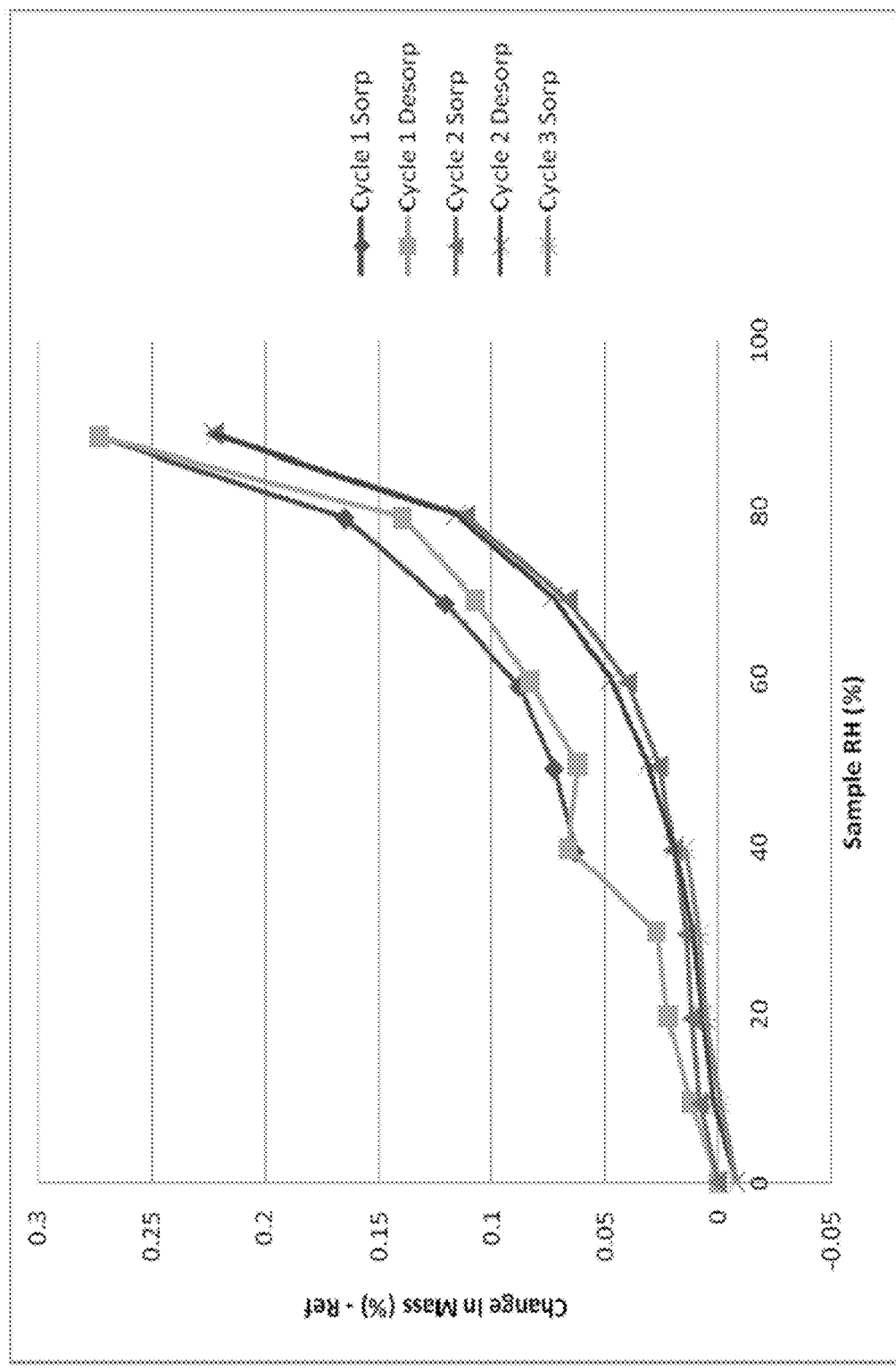
Fig. 32: GVS Isotherm Graph for the 1:1 Cilostazol 2,4-Dihydroxybenzoic Acid Cocrystal

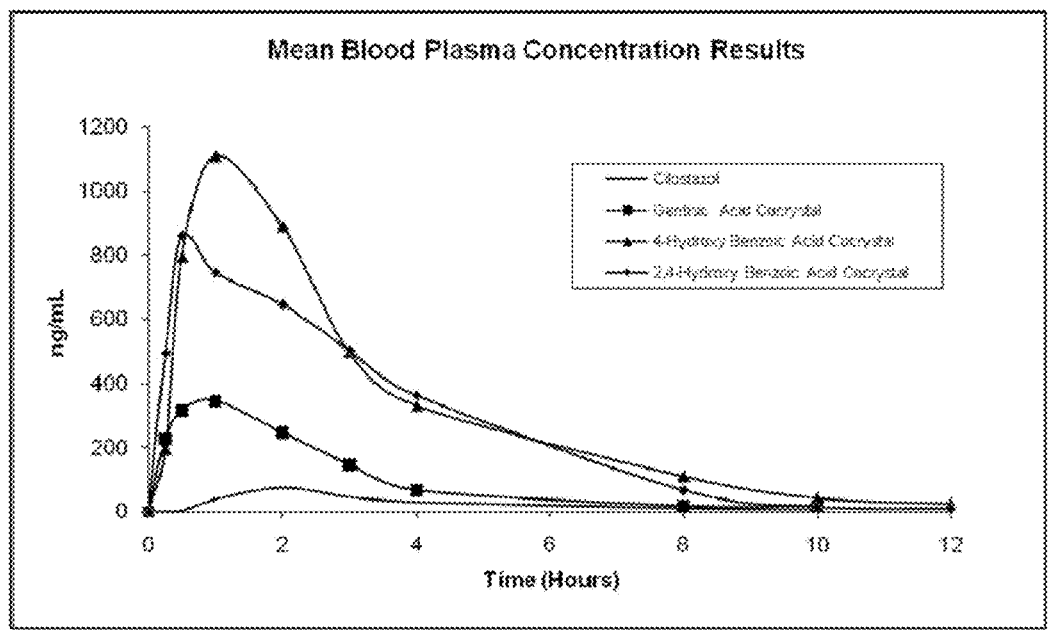
Figure 33: Mean blood plasma concentration-time profiles from the pharmacokinetic study of Example 5

CILOSTAZOL COCRYSTALS AND COMPOSITIONS

CROSS-REFERENCE TO RELATED APPLICATIONS

This application claim priority to PCT International Application No. PCT/IB2011/001430, filed Apr. 28, 2011, which claims priority to U.S. patent application 61/328,827, filed Apr. 28, 2010, and to U.S. patent application 61/452,363, filed Mar. 14, 2011; the disclosures of which are incorporated herein by reference.

FIELD OF INVENTION

The invention relates to new crystalline compounds containing cilostazol, more particularly, the invention relates to cilostazol compositions and cocrystals, therapeutic uses of those cilostazol compositions and cocrystals, and pharmaceutical compositions containing them.

BACKGROUND

Cilostazol, 6-[4-(1-cyclohexyl-1H-tetrazol-5-yl)butoxy]-3,4-dihydro-2(1H)-quinolinone, shown below, is a cyclic AMP phosphodiesterase III inhibitor.

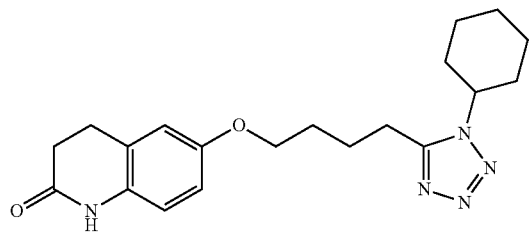 [SMILES: O=C1CCc2cc(OCCCCc3nnnn3C3CCCCC3)ccc2N1]

Cilostazol is a white to off white crystalline powder that is slightly soluble in methanol and ethanol, but is practically insoluble in water, 0.1N HCl and 0.1N NaOH. Cilostazol is further described at Monograph no. 2298 of the Merck Index (Thirteenth Edition, 2001) and is also identified by CAS Registry Number: 73963-72-1. Preparation of cilostazol is described by Nishi et al. in Chem. Pharm. Bull. 31, 1151 (1983) and in U.S. Pat. No. 4,277,479.

Cilostazol exhibits high inhibitory action for platelet aggregation as well as phosphodiesterase inhibition, antiulcer activity, hypotensive action, antiphlogistic action, anti-inflammatory action, etc. As an anti-platelet agent, a vasodilator, phosphodiesterase inhibitor, and a platelet aggregation inhibitor cilostazol has been shown to be an effective drug for the prevention and treatment of ischemic symptoms caused by chronic arterial occlusion such as intermittent claudication. Cilostazol has efficacy for improving various ischemic conditions such as ulcer, pain and coldness that are based on chronic arterial occlusion. Although its mechanism of action is not entirely clear, cilostazol inhibits phosphodiesterase III and suppresses cAMP degradation. These events result in increased levels of cAMP in platelets and blood vessels, leading to inhibition of platelet aggregation and vasodilation. In addition to its reported vasodilator and anti-platelet effects, cilostazol reduces the ability of blood to clot and has been proposed to have beneficial effects on plasma lipoproteins. By inhibiting the blood platelets from coagulating or aggregating, blood flow is enhanced and increased. Cilostazol has also been approved as a medicament having an indication for improving cerebral circulation which prevents the relapse after treatment of cerebral infarction (except cardiogenic cerebral infarction) (JP-A-56 (1981)-49378).

Cilostazol and its various uses have been described in U.S. Pat. No. 4,277,479, "Tetrazolylalkoxycarbostyril Derivatives and Pharmaceutical Compositions Containing Them"; U.S. Pat. No. 6,187,790, "Use of Cilostazol for Treatment of Sexual Dysfunction"; U.S. Pat. No. 6,515,128, "Processes for Preparing Cilostazol"; U.S. Pat. Nos. 6,531,603, 6,573,382, 6,531,603, 6,657,061, and 6,660,864, "Polymorphic Forms of 6-[4-1(1-Cyclohexyl-1H-tetrazol-5-yl)Butoxy]-3,4-Dihydro-2(1H)-Quinolinone"; U.S. Pat. Nos. 6,525,201, 6,660,773, and 6,740,758, "Processes for Preparing 6-Hydroxy-3,4-Dihydroquinolinone, Cilostazol and N-(4-Methoxyphenyl)-3-Chloropropionamide", and U.S. Pat. No. 6,825,214, "Substantially Pure Cilostazol and Processes for Making Same." Formulations of cilostazol and their therapeutic uses are disclosed, for example, in WO 2009/113,741; WO 2009/107,864; and U.S. Published application US 2009/0297596. All of these documents are incorporated herein by reference.

Cilostazol is marketed as 50 mg and 100 mg tablets by Otsuka Pharmaceutical Co., Ltd under the PLETAL® tradename. Cilostazol is classified by the Biopharmaceutical Classification System (BCS) as a Class II drug, indicating that it is a low solubility, high permeability drug. This signifies that the rate limiting step for oral bioavailability of cilostazol is the dissolution of the drug from its pharmaceutical dosage form.

Although therapeutic efficacy is the primary concern for an active pharmaceutical ingredient (API), the salt and solid state form (i.e., the crystalline or amorphous form) of a drug candidate can be critical to its pharmacological properties, such as bioavailability, and to its development as a viable API. Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate solid state form for further drug development can reduce the time and the cost of that development.

Obtaining crystalline forms of an API is extremely useful in drug development. It permits better characterization of the drug candidate's chemical and physical properties. It is also possible to achieve desired properties of a particular API by forming a cocrystal of the API and a coformer. Crystalline forms often have better chemical and physical properties than the free base in its amorphous state. Such crystalline forms may, as with the cocrystals of the invention, possess more favorable pharmaceutical and pharmacological properties or be easier to process than known forms of the API itself. For example, a cocrystal may have different dissolution and solubility properties than the API itself and can be used to deliver APIs therapeutically. New drug formulations comprising cocrystals of a given API may have superior properties over its existing drug formulations. They may also have better storage stability.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

A cocrystal of an API is a distinct chemical composition of the API and a coformer which generally possesses distinct crystallographic and spectroscopic properties when compared to those of the API and coformer individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC).

SUMMARY

The invention relates to new compositions and cocrystals of cilostazol, which have improved physiochemical and/or pharmaceutical properties over cilostazol itself. The invention also relates to therapeutic compositions containing compositions and cocrystals of cilostazol as well as methods of treating or preventing disorders relating to platelet aggregation, phosphodiesterase inhibition and/or ischemic conditions with compositions and cocrystals of cilostazol.

BRIEF DESCRIPTION OF FIGURES

FIG. 1 shows an XRPD pattern for the 1:1 cilostazol gentisic acid cocrystal.

FIG. 2 shows an ORTEP drawing of the 1:1 cilostazol gentisic acid cocrystal.

FIG. 3 shows a packing diagram of the 1:1 cilostazol gentisic acid cocrystal.

FIG. 4 shows a calculated XRPD pattern for the 1:1 cilostazol gentisic acid cocrystal.

FIG. 5 shows a DSC trace for the 1:1 cilostazol gentisic acid cocrystal.

FIG. 6 shows a TGA trace for the 1:1 cilostazol:gentisic acid cocrystal.

FIG. 7 shows the $^1$H NMR spectrum of the 1:1 cilostazol gentisic acid cocrystal.

FIG. 8 shows the GVS isotherm graph for the 1:1 cilostazol gentisic acid cocrystal.

FIG. 9 shows an XRPD pattern for the 1:1:1 cilostazol gentisic acid $H_2O$ cocrystal FIG. 10 shows an ORTEP drawing of the 1:1:1 cilostazol gentisic acid $H_2O$ cocrystal.

FIG. 11 shows a packing diagram of the 1:1:1 cilostazol gentisic acid $H_2O$ cocrystal.

FIG. 12 shows a calculated XRPD pattern for the 1:1:1 cilostazol gentisic acid $H_2O$ cocrystal.

FIG. 13 shows a DSC trace for the 1:1:1 cilostazol gentisic acid $H_2O$ cocrystal.

FIG. 14 shows a TGA trace for the 1:1:1 cilostazol gentisic acid $H_2O$ cocrystal.

FIG. 15 shows the $^1$H NMR spectrum of the 1:1:1 cilostazol gentisic acid $H_2O$ cocrystal.

FIG. 16 shows the GVS isotherm graph for the 1:1:1 cilostazol gentisic acid $H_2O$ cocrystal.

FIG. 17 shows an XRPD pattern for the 1:1 cilostazol 4-hydroxybenzoic acid cocrystal.

FIG. 18 shows an ORTEP drawing of the 1:1 cilostazol 4-hydroxybenzoic acid cocrystal.

FIG. 19 shows a packing diagram of the 1:1 cilostazol 4-hydroxybenzoic acid cocrystal.

FIG. 20 shows a calculated XRPD pattern for the 1:1 cilostazol 4-hydroxybenzoic acid cocrystal.

FIG. 21 shows a DSC trace for the 1:1 cilostazol 4-hydroxybenzoic acid cocrystal.

FIG. 22 shows a TGA trace for the 1:1 cilostazol 4-hydroxybenzoic acid cocrystal.

FIG. 23 shows the $^1$H NMR spectrum of the 1:1 cilostazol 4-hydroxybenzoic acid cocrystal.

FIG. 24 shows the GVS isotherm graph for the 1:1 cilostazol 4-hydroxybenzoic acid cocrystal.

FIG. 25 shows an XRPD pattern for the 1:1 cilostazol 2,4-dihydroxybenzoic acid cocrystal.

FIG. 26 shows an ORTEP drawing of the 1:1 cilostazol 2,4-dihydroxybenzoic acid cocrystal.

FIG. 27 shows a packing diagram of the 1:1 cilostazol 2,4-dihydroxybenzoic acid cocrystal.

FIG. 28 shows a calculated XRPD pattern for the 1:1 cilostazol 2,4-dihydroxybenzoic acid cocrystal.

FIG. 29 shows a DSC trace for the 1:1 cilostazol 2,4-dihydroxybenzoic acid cocrystal.

FIG. 30 shows a TGA trace for the 1:1 cilostazol 2,4-dihydroxybenzoic acid cocrystal.

FIG. 31 shows the $^1$H NMR spectrum of the 1:1 cilostazol 2,4-dihydroxybenzoic acid cocrystal.

FIG. 32 shows the GVS isotherm graph for the 1:1 cilostazol 2,4-dihydroxybenzoic acid cocrystal.

FIG. 33 shows the mean blood plasma concentration-time profiles from the pharmacokinetic study of Example 5.

DETAILED DESCRIPTION

The invention relates to improvements of the physiochemical and/or the pharmaceutical properties of cilostazol. Disclosed herein are several new cocrystals of cilostazol which represent new compositions of cilostazol, including: a 1:1 cilostazol gentisic acid cocrystal, a 1:1:1 cilostazol gentisic acid $H_2O$ cocrystal, a 1:1 cilostazol 4-hydroxybenzoic acid cocrystal, and a 1:1 cilostazol 2,4-dihydroxybenzoic acid cocrystal. The therapeutic uses of these cilostazol cocrystals and compositions are described as well as therapeutic compositions containing them. The cocrystals and the methods used to characterize them are described below. In the description herein, discussion of a cilostazol cocrystal of the invention refers not only to the cocrystal itself but also to the corresponding composition of cilostazol and the associated coformer(s).

Therapeutic Uses of the Cilostazol Cocrystals

The invention further relates to the therapeutic use of at least one cilostazol cocrystal of the invention to treat or prevent disorders relating to platelet aggregation, phosphodiesterase inhibition and/or ischemic conditions such as those discussed above. Accordingly, the invention relates to method of treating such a disorder comprising the step of administering to a patient in need thereof a therapeutically effective amount of at least one cilostazol cocrystal of the invention or of a therapeutic composition containing at least one cilostazol cocrystal.

The term "treatment" or "treating" means any treatment of a condition or disorder in a mammal, including: preventing or protecting against the condition or disorder, that is, causing the clinical symptoms not to develop; inhibiting the condition or disorder, that is, arresting or suppressing the development of clinical symptoms; and/or relieving the condition or disorder (including the relief of pain associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the condition or disorder. The term "protection" is meant to include "prophylaxis."

Pharmaceutical Compositions Containing Cilostazol Cocrystals

The invention also relates to pharmaceutical compositions comprising a therapeutically effective amount of at least one cilostazol cocrystal according to the invention and a pharmaceutically acceptable carrier (also known as a pharmaceutically acceptable excipient). As mentioned above, these pharmaceutical compositions are therapeutically useful to treat or prevent disorders relating to platelet aggregation, phosphodiesterase inhibition and/or ischemic symptoms such as those discussed above.

A pharmaceutical composition of the invention may be in any pharmaceutical form which contains at least one cilostazol cocrystal according to the invention. The pharmaceutical composition may be, for example, a tablet, capsule, liquid suspension, injectable, topical, or transdermal. The pharmaceutical compositions generally contain, for example, about 1% to about 99% by weight of at least one cilostazol cocrystal of the invention and, for example, 99% to 1% by weight of at least one suitable pharmaceutical excipient. In one embodiment, the composition may be between about 5% and about 75% by weight of at least one cilostazol cocrystal of the invention with the rest being at least one suitable pharmaceutical excipient or at least one other adjuvant, as discussed below.

A "therapeutically effective amount of at least one cilostazol cocrystal according to the invention" is that which correlates to about 25-about 250 mg of cilostazol itself. As discussed above, cilostazol is marketed as 50 mg and 100 mg tablets by Otsuka Pharmaceutical Co., Ltd under the PLETAL® tradename. Typical doses are about 100 mg twice a day for intermittent claudication. The actual amount required for treatment of any particular condition or disorder or any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of cilostazol; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, one having at least one cilostazol cocrystal of the invention, a carrier should be chosen that maintains the crystalline form. In other words, in a pharmaceutical composition administering a cilostazol composition of the invention in its crystalline form, the carrier should not substantially alter the cilostazol cocrystal. Nor should the carrier be otherwise incompatible with the cilostazol cocrystal or composition used, such as by producing any undesirable biological effect or otherwise interacting in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, at least one cilostazol cocrystal may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing at least one cilostazol cocrystal according to the present disclosure with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Because the cilostazol cocrystal is maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). The cilostazol cocrystals according to the invention may also be used as precursors in the formulation of liquid pharmaceutical compositions. Administration of the cilostazol cocrystals in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

EXAMPLES

The following analytical methods were used to characterize the cilostazol cocrystals of the invention:

X-Ray Powder Diffraction:

X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 2° to 42° 2Θ using a step size of 0.05° 2Θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analyzed using Diffrac Plus EVA v11.0.0.2 or v13.0.0.2.

Single Crystal X-Ray Diffraction (SCXRD):

Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning Calorimetry (DSC):

DSC data was collected on a TA instruments Q2000 equipped with a 50 position autosampler. The calibration for thermal capacity was carried out using sapphire and the calibration for the energy and temperature was carried out using certified indium. Typically 0.8-1.2 mg of each sample, in a pin-holed aluminium pan, was heated at 10° C./min from 25° C. to 350° C. A purge of dry nitrogen at 50 ml/min was maintained over the sample. The instrument control software was Advantage for Q series v2.8.0.392 and Thermal Advantage v4.8.3. All data analysis was performed using Universal Analysis v4.3A software.

Thermo-Gravimetric Analysis (TGA):

TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C./min from ambient temperature to 350° C. A nitrogen purge at 60 ml/min was maintained over the sample. The instrument control software was Advantage for Q Series v2.8.0.392 and Thermal Advantage v4.8.3

Solution Proton NMR:

$^1$H-NMR spectra were recorded on a Bruker 400 MHz spectrometer equipped with an auto-sampler and controlled by a DRX400 console. The samples were dissolved in d6-DMSO for analysis. The data was acquired using ICON-NMR v4.0.4 (build 1) running with Topspin v1.3 (patch level 8) using the standard Bruker loaded experiments.

Water Content Determination by Karl Fischer Titration (KF):

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and triplicate determinations were made.

Gravimetric Vapour Isotherm (GVS) Analysis:

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 ml·min$^{-1}$ The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined in Table 1 (2 scans giving 1 complete cycle). The standard isotherm was performed at 25° C. at 10% RH intervals over a 0.5-90% RH range. Data analysis was undertaken in Microsoft Excel using DVS Analysis Suite v6.0.0.7. The sample was recovered after completion of the isotherm and re-analyzed by XRPD.

TABLE 1

| Method Parameters for SMS DVS Intrinsic Experiments | |
|---|---|
| Parameters | Values |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml · min$^{-1}$) | 200 |
| Temperature (° C.) | 25 |

TABLE 1-continued

Method Parameters for SMS DVS Intrinsic Experiments

| Parameters | Values |
| --- | --- |
| Stability (° C. min$^{-1}$) | 0.2 |
| Sorption Time (hours) | 6 hour time out |

Example 1

1:1 Cilostazol Gentisic Acid Cocrystal

1.1 Preparation of a 1:1 Cilostazol Gentisic Acid Cocrystal

Cilostazol (400 mg) was weighed into a glass vial. 2 ml of a hot saturated solution of gentisic acid in methyl ethyl ketone was then added to the vial. The resulting slurry was placed in a shaker and matured for 5 days (RT to 50° C. on an 8 hour cycle, heating to 50° C. for 4 hours and then cooling to RT for a further 4 hours). The product was then filtered under vacuum for ca. 1 hour before being allowed to dry under ambient conditions overnight.

1.2 XRPD Characterisation of a 1:1 Cilostazol Gentisic Acid Cocrystal

The experimental XRPD pattern of the 1:1 cilostazol gentisic acid cocrystal is shown in FIG. 1. Table 2 lists the angles, °2θ±0.2°2θ, and d-spacing of the peaks identified in the XRPD pattern of FIG. 1. The entire list of peaks, or a subset thereof, may be sufficient to characterise the cocrystal. For example, the cocrystal may be characterised by at least five peaks selected from the peaks at 3.5, 6.9, 10.4, 16.5, 17.3, 17.8, 20.5, 22.0, 23.0, and 23.6 °2θ±0.2°2θ as well as by a XRPD pattern substantially similar to FIG. 1.

TABLE 2

| Angle °2θ ± 0.2 °2θ | d value Angstrom | Intensity % |
| --- | --- | --- |
| 3.5 | 25.57 | 58.40 |
| 6.9 | 12.82 | 3.00 |
| 10.4 | 8.54 | 100.00 |
| 11.8 | 7.50 | 2.20 |
| 11.9 | 7.43 | 1.80 |
| 13.1 | 6.73 | 1.00 |
| 13.3 | 6.63 | 1.50 |
| 14.1 | 6.26 | 1.80 |
| 14.9 | 5.94 | 0.90 |
| 15.2 | 5.83 | 2.10 |
| 15.8 | 5.59 | 1.00 |
| 16.5 | 5.36 | 2.20 |
| 17.3 | 5.12 | 14.20 |
| 17.7 | 5.01 | 7.60 |
| 19.6 | 4.52 | 0.90 |
| 20.5 | 4.33 | 10.30 |
| 20.8 | 4.27 | 19.50 |
| 21.0 | 4.22 | 1.70 |
| 22.0 | 4.03 | 2.20 |
| 23.0 | 3.87 | 13.50 |
| 23.6 | 3.77 | 20.30 |
| 24.0 | 3.71 | 2.10 |
| 24.3 | 3.66 | 7.40 |
| 26.2 | 3.39 | 1.10 |
| 26.6 | 3.34 | 4.90 |
| 27.1 | 3.29 | 3.10 |
| 27.8 | 3.20 | 6.90 |
| 31.4 | 2.84 | 1.50 |
| 32.7 | 2.73 | 1.10 |

TABLE 2-continued

| Angle °2θ ± 0.2 °2θ | d value Angstrom | Intensity % |
| --- | --- | --- |
| 33.2 | 2.70 | 2.00 |
| 33.7 | 2.66 | 1.00 |
| 34.0 | 2.63 | 1.40 |
| 37.1 | 2.42 | 1.00 |

1.3 SCXRD Characterisation of a 1:1 Cilostazol Gentisic Acid Cocrystal

The crystal used for single crystal structure determination was prepared as follows: Cilostazol (500 mg) and gentisic acid (209 mg) were weighed into a glass vial. Nitromethane (2 ml) was added to the vial and the vial was sealed. The resulting slurry was placed in a shaker and matured for 5 days (RT to 50° C. on an 8 hour cycle, heating to 50° C. for 4 hours and then cooling to RT for a further 4 hours). The product was then filtered under vacuum for ca. 1 hour before being allowed to dry under ambient conditions overnight. A suitable single crystal was isolated from the batch and used for SCXRD analysis.

The single crystal data and structure refinement parameters are reported in Table 3. FIG. 2 shows an ORTEP drawing of the asymmetric unit from the crystal structure of the 1:1 cilostazol gentisic acid cocrystal showing the atom numbering scheme employed. Anisotropic atomic displacement ellipsoids for the non-hydrogen atoms are shown at the 50% probability level and hydrogen atoms are displayed as spheres of arbitrary radius. FIG. 3 shows the crystal packing of the 1:1 cilostazol gentisic acid cocrystal; the view is down the a-axis of the unit cell. The calculated XRPD pattern based on the single crystal data and structure for the 1:1 cilostazol gentisic acid cocrystal is shown in FIG. 4. It is also noted that there are some small temperature shifts in some of the peaks owing to the fact that the experimental XRPD pattern was collected at room temperature and the calculated XRPD pattern is derived from data collected at 100K. There are also small intensity differences owing to preferred orientation effects, present in the experimental pattern.

TABLE 3

| | |
| --- | --- |
| Molecular formula | $C_{27}H_{33}N_5O_6$ |
| Molecular weight | 523.58 |
| Crystal System | Triclinic |
| Space Group | P-1 |
| Unit Cell Dimensions | a = 6.5528(3) Å |
| | b = 8.0562(3) Å |
| | c = 25.5472(12) Å |
| | α = 89.086(4)° |
| | β = 83.993(4)° |
| | γ = 73.079(4)° |
| Cell Volume | 1283.03(10) Å$^3$ |
| Z | 2 |
| Temperature | 100 (2) K |
| Radiation Wavelength/type | 1.54178 Å/CuKα |
| Goodness of fit | 1.045 |
| R factor | 0.0355 |
| Morphology | Colourless prism |

1.4 DSC of 1:1 Cilostazol Gentisic Acid Cocrystal

The differential scanning calorimetry (DSC) trace, FIG. 5, shows a single endotherm with an onset temperature of 118.94° C. and a peak maximum of 122.30° C.

1.5 TGA of 1:1 Cilostazol Gentisic Acid Cocrystal

The thermal gravimetric analysis (TGA) trace, FIG. 6, shows no significant weight loss prior to degradation with 99.87% remaining at 175.0° C.

1.6 $^1$H NMR Spectrum of a 1:1 Cilostazol Gentisic Acid Cocrystal $^1$H NMR spectrum of the 1:1 cilostazol gentisic acid cocrystal, shown in FIG. 7, displays the following peaks: $^1$H NMR (400 MHz, d6-DMSO) δ: 9.92 (1H), 9.16 (1H), 7.15 (1H), 6.96 (1H) 6.76 (4H), 4.40 (1H), 3.96 (2H), 2.97 (2H), 2.82 (2H), 2.39 (2H), 1.66-1.97 (11H), 1.45 (2H), 1.26 (1H). The peak at 7.16 ppm in the $^1$H NMR spectrum corresponds to one proton on the aromatic ring of the gentisic acid. Comparison of the integration of this peak with that at 4.40 ppm, which corresponds to one CH proton of the cyclohexyl ring of cilostazol, indicates that the cocrystal has an API:coformer stoichiometry of 1:1.

1.7 Karl Fischer Titration of the 1:1 Cilostazol Gentisic Acid Cocrystal

Karl Fischer analysis of the 1:1 cilostazol gentisic acid cocrystal was carried out in triplicate and the result was 0.2% water content in all three analyses, confirming that the cocrystal is anhydrous.

1.8 Gravimetric Vapour Sorption (GVS) Analysis of the 1:1 Cilostazol Gentisic Acid Cocrystal The moisture sorption isotherm graph obtained for the 1:1 cilostazol gentisic acid cocrystal is shown in FIG. 8. The cocrystal was found to reversibly adsorb <0.3% w/w across the 0-90% relative humidity range at 25° C. under nitrogen. This shows that the cocrystal in not hygroscopic and does not convert to the 1:1:1 cilostazol gentisic acid H$_2$O cocrystal under raised relative humidity levels. XRPD analysis after completion of the isotherm confirmed that the cocrystal was unchanged.

1.9 Gram Scale Preparation of the 1:1 Cilostazol Gentisic Acid Cocrystal

Cilostazol (3.00 g) was placed in a round bottom flask. 20 ml of a saturated solution of gentisic acid in methyl ethyl ketone was added. With stirring the resultant slurry was gradually heated using a water bath to approximately 60° C. After about 30 minutes the water bath was removed and the slurry was stirred at room temperature for a further 3 days before the product was filtered under vacuum and air dried overnight. XRPD analysis confirmed the product to be the 1:1 cilostazol gentisic acid cocrystal.

Example 2

1:1:1 Cilostazol Gentisic Acid H$_2$O Cocrystal

2.1 Preparation of a 1:1:1 Cilostazol Gentisic Acid H$_2$O Cocrystal

Cilostazol (300 mg) and gentisic acid (125 mg) were weighed into a glass vial. Nitromethane (1 ml) and water (1 ml) were added to the vial. The resulting slurry was placed in a shaker and matured for 5 days (RT to 50° C. on an 8 hour cycle, heating to 50° C. for 4 hours and then cooling to RT for a further 4 hours). The product was then filtered under vacuum for ca. 1 hour and then left to dry under ambient conditions overnight.

2.2 XRPD Characterisation of a 1:1:1 Cilostazol Gentisic Acid H$_2$O Cocrystal The experimental XRPD pattern of the 1:1:1 cilostazol gentisic acid H$_2$O cocrystal is shown in FIG. 9. Table 4 lists the angles, °2θ±0.2°2θ, and d-spacing of the peaks identified in the XRPD pattern of FIG. 9. The entire list of peaks, or a subset thereof, may be sufficient to characterise the cocrystal. For example, the cocrystal may be characterised by at least five peaks selected from the peaks at 5.1, 7.9, 10.1, 12.6, 14.8, 16.9, 18.2, 22.8, 24.9 and 25.5 °2θ±0.2°2θ as well as by a XRPD pattern substantially similar to FIG. 9.

TABLE 4

| Angle °2θ ± 0.2 °2θ | d value Angstrom | Intensity % |
| --- | --- | --- |
| 5.1 | 17.28 | 56.70 |
| 7.9 | 11.12 | 2.90 |
| 9.1 | 9.76 | 0.90 |
| 10.1 | 8.74 | 19.40 |
| 10.7 | 8.26 | 1.00 |
| 12.6 | 7.01 | 6.20 |
| 13.5 | 6.57 | 0.70 |
| 14.2 | 6.24 | 0.70 |
| 14.8 | 6.00 | 16.30 |
| 15.1 | 5.87 | 100.00 |
| 16.1 | 5.49 | 0.70 |
| 16.9 | 5.24 | 11.90 |
| 18.2 | 4.87 | 5.20 |
| 19.8 | 4.48 | 4.90 |
| 20.2 | 4.40 | 8.80 |
| 20.3 | 4.36 | 11.10 |
| 20.6 | 4.30 | 4.40 |
| 21.5 | 4.12 | 17.10 |
| 21.7 | 4.08 | 12.10 |
| 22.1 | 4.01 | 7.90 |
| 22.8 | 3.89 | 13.80 |
| 23.4 | 3.80 | 19.90 |
| 23.4 | 3.79 | 22.30 |
| 24.0 | 3.70 | 2.40 |
| 24.9 | 3.57 | 12.70 |
| 25.5 | 3.49 | 11.00 |
| 26.3 | 3.39 | 1.70 |
| 26.7 | 3.33 | 1.90 |
| 27.4 | 3.26 | 2.10 |
| 27.6 | 3.23 | 2.60 |
| 28.8 | 3.09 | 4.30 |
| 29.0 | 3.08 | 5.90 |
| 30.6 | 2.92 | 3.90 |
| 31.1 | 2.87 | 0.80 |
| 31.9 | 2.81 | 1.10 |
| 32.0 | 2.79 | 1.10 |
| 32.7 | 2.74 | 1.70 |
| 33.3 | 2.69 | 5.50 |
| 34.2 | 2.62 | 1.50 |
| 34.7 | 2.58 | 1.10 |
| 35.5 | 2.53 | 1.40 |
| 35.9 | 2.50 | 0.90 |
| 36.8 | 2.44 | 1.00 |
| 38.6 | 2.33 | 1.30 |
| 41.3 | 2.18 | 7.60 |

2.3 SCXRD Characterisation of a 1:1:1 Cilostazol Gentisic Acid H$_2$O Cocrystal The crystal used for single crystal structure determination was prepared as follows: Cilostazol (500 mg) and gentisic acid (209.4 mg) were weighed into a glass vial. Nitromethane (1.65 ml) was added to the vial. The resulting slurry was placed in a shaker and matured for 7 days (RT to 50° C. on an 8 hour cycle, heating to 50° C. for 4 hours and then cooling to RT for a further 4 hours). The product was then filtered under vacuum before being allowed to dry under ambient conditions overnight. Approximately 10 mg (estimated by eye) was added into a glass vial and enough nitromethane was added to give a suspension. The vial was placed in a shaker at 50° C. for 4 hours before being filtered into a clean glass vial. The hot solution was allowed to slowly cool down (5° C. every ten minutes), resulting in a clear solution at room temperature. The vial was covered with film which was then pierced to allow slow evaporation and crystal formation. Post 24 hours a crystal suitable for SCXRD was isolated.

The single crystal data and structure refinement parameters are reported in Table 5. FIG. 10 shows an ORTEP drawing of the asymmetric unit from the crystal structure of the cilostazol gentisic acid $H_2O$ cocrystal showing the atom numbering scheme employed. FIG. 10 shows that the water molecule, $H_2O$, present in this cocrystal acts a second coformer participating in the structure of the cocrystal. Anisotropic atomic displacement ellipsoids for the non-hydrogen atoms are shown at the 50% probability level and hydrogen atoms are displayed as spheres of arbitrary radius. FIG. 11 shows the crystal packing of the 1:1:1 cilostazol gentisic acid $H_2O$ cocrystal; the view is down the a-axis of the unit cell. The calculated XRPD pattern based on the single crystal data and structure for the 1:1:1 cilostazol gentisic acid $H_2O$ cocrystal is shown in FIG. 12. It is also noted that there are some small temperature shifts in some of the peaks owing to the fact that the experimental XRPD pattern was collected at room temperature and the calculated XRPD pattern is derived from data collected at 120K. There are also small intensity differences owing to preferred orientation effects, present in the experimental pattern.

TABLE 5

| | |
|---|---|
| Molecular formula | $C_{27}H_{35}N_5O_7$ |
| Molecular weight | 541.60 |
| Crystal System | Monoclinic |
| Space Group | P21/n |
| Unit Cell Dimensions | a = 6.6287(3) Å |
| | b = 34.531(2) Å |
| | c = 11.6203(8) Å |
| | α = 90.00° |
| | β = 90.155(6)° |
| | γ = 90.00° |
| Cell Volume | 2659.9(3) Å³ |
| Z | 4 |
| Temperature | 120 (2) K |
| Radiation Wavelength/type | 0.71073 Å/MoKα |
| Goodness of fit | 1.007 |
| R factor | 0.0683 |
| Morphology | Colourless lath |

2.4 DSC of 1:1:1 Cilostazol Gentisic Acid $H_2O$ Cocrystal

The differential scanning calorimetry (DSC) trace, FIG. 13, shows a broad endotherm over the temperature range 70-117° C.

2.5 TGA of 1:1:1 Cilostazol Gentisic Acid $H_2O$ Cocrystal

In the thermal gravimetric analysis (TGA) trace, FIG. 14, it can be seen that there is a weight loss of around 3.3% over the temperature range 70-117° C. This weight loss corresponds to one mole of water.

2.6 $^1H$ NMR Spectrum of a 1:1:1 Cilostazol Gentisic Acid $H_2O$ Cocrystal

The $^1H$ NMR spectrum of the 1:1:1 cilostazol gentisic acid $H_2O$ cocrystal, shown in FIG. 15, displays the following peaks: $^1H$ NMR (400 MHz, d6-DMSO) δ: 9.92 (1H), 9.16 (1H), 7.16 (1H), 6.96 (1H) 6.77 (4H), 4.40 (1H), 3.96 (2H), 2.97 (2H), 2.82 (2H), 2.39 (2H), 1.66-1.98 (11H), 1.43 (2H), 1.25 (1H). The peak at 7.16 ppm in the $^1H$ NMR spectrum corresponds to one proton on the aromatic ring of the gentisic acid. Comparison of the integration of this peak with that at 4.40 ppm, which corresponds to one CH proton of the cyclohexyl ring of cilostazol, indicates that the cocrystal has an API:gentisic acid stoichiometry of 1:1.

2.7 Gravimetric Vapour Sorption (GVS) Analysis of the 1:1:1 Cilostazol Gentisic Acid $H_2O$ Cocrystal The moisture sorption isotherm graph obtained for the 1:1:1 cilostazol gentisic acid $H_2O$ cocrystal is shown in FIG. 16. The cocrystal was found to reversibly adsorb only 0.1% w/w across the 0-90% relative humidity range at 25° C. under nitrogen. This shows that the cocrystal in not hygroscopic and does not dehydrate as the relative humidity levels are lowered to 0%. XRPD analysis after completion of the isotherm confirmed that the cocrystal was unchanged.

Example 3

1:1 Cilostazol 4-Hydroxybenzoic Acid Cocrystal 3.1 Preparation of a 1:1 Cilostazol 4-Hydroxybenzoic Acid Cocrystal Cilostazol (300 mg) and 4-hydroxybenzoic acid (112 mg) were weighed into a glass vial. Nitromethane (1.5 ml) was added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour before being allowed to dry under ambient conditions overnight.

3.2 XRPD Characterisation of 1:1 Cilostazol 4-Hydroxybenzoic Acid Cocrystal

The experimental XRPD pattern of the 1:1 cilostazol 4-hydroxybenzoic acid cocrystal is shown in FIG. 17. Table 6 lists the angles, °2θ±0.2°2θ, and d-spacing of the peaks identified in the XRPD pattern of FIG. 17. The entire list of peaks, or a subset thereof, may be sufficient to characterise the cocrystal. For example, the cocrystal may be characterised by at least five peaks selected from the peaks at 11.2, 12.8, 14.3, 15.7, 18.0, 19.3, 20.9, 21.5, 22.0 and 26.0 °2θ±0.2°2θ as well as by a XRPD pattern substantially similar to FIG. 17.

TABLE 6

| Angle °2θ ± 0.2 °2θ | d value Angstrom | Intensity % |
|---|---|---|
| 8.3 | 10.63 | 5.90 |
| 8.6 | 10.33 | 4.30 |
| 9.0 | 9.83 | 3.80 |
| 11.2 | 7.92 | 8.20 |
| 11.4 | 7.72 | 3.10 |
| 12.8 | 6.89 | 6.60 |
| 14.0 | 6.31 | 9.90 |
| 14.3 | 6.21 | 27.20 |

TABLE 6-continued

| Angle °2θ ± 0.2 °2θ | d value Angstrom | Intensity % |
|---|---|---|
| 14.9 | 5.94 | 4.80 |
| 15.4 | 5.75 | 6.50 |
| 15.7 | 5.64 | 13.60 |
| 16.6 | 5.33 | 44.60 |
| 16.8 | 5.26 | 49.60 |
| 18.0 | 4.91 | 52.50 |
| 18.7 | 4.73 | 4.80 |
| 19.0 | 4.67 | 14.00 |
| 19.3 | 4.60 | 15.20 |
| 19.8 | 4.48 | 40.40 |
| 20.0 | 4.43 | 100.00 |
| 20.9 | 4.24 | 9.60 |
| 21.5 | 4.12 | 11.40 |
| 22.0 | 4.04 | 94.10 |
| 22.6 | 3.94 | 13.60 |
| 22.8 | 3.90 | 6.60 |
| 23.2 | 3.83 | 45.20 |
| 23.3 | 3.81 | 61.10 |
| 24.1 | 3.69 | 20.30 |
| 24.3 | 3.65 | 18.60 |
| 25.2 | 3.54 | 6.90 |
| 25.6 | 3.47 | 11.00 |
| 25.8 | 3.46 | 11.70 |
| 26.0 | 3.43 | 93.10 |
| 26.3 | 3.38 | 13.00 |
| 27.1 | 3.29 | 1.90 |
| 27.4 | 3.25 | 4.80 |
| 27.9 | 3.19 | 7.70 |
| 28.2 | 3.16 | 13.50 |
| 28.8 | 3.09 | 2.80 |
| 29.2 | 3.06 | 13.80 |
| 29.5 | 3.03 | 2.90 |
| 29.8 | 3.00 | 2.40 |
| 30.2 | 2.96 | 12.50 |
| 30.7 | 2.91 | 4.80 |
| 30.9 | 2.89 | 11.40 |
| 31.3 | 2.86 | 3.20 |
| 31.6 | 2.83 | 9.40 |
| 31.7 | 2.82 | 9.40 |
| 32.2 | 2.78 | 4.80 |
| 32.7 | 2.74 | 4.00 |
| 33.4 | 2.68 | 3.70 |
| 33.8 | 2.65 | 5.60 |
| 34.2 | 2.62 | 4.90 |
| 35.1 | 2.56 | 5.70 |
| 35.8 | 2.51 | 5.80 |
| 36.2 | 2.48 | 2.60 |
| 36.8 | 2.44 | 2.80 |
| 37.1 | 2.42 | 5.80 |
| 37.9 | 2.37 | 3.40 |
| 38.6 | 2.33 | 4.60 |
| 38.9 | 2.32 | 5.60 |
| 39.3 | 2.29 | 3.30 |
| 39.7 | 2.27 | 2.00 |

3.3 SCXRD Characterisation of a 1:1 Cilostazol 4-Hydroxybenzoic acid Cocrystal The crystal used for single crystal structure determination was prepared as follows: Cilostazol (100 mg) and 4-hydroxybenzoic acid (37.4 mg) were placed in a stainless steel ball mill. Water (2 drops) was added. The chemicals were ground together for 60 minutes at 20 Hz. The product was removed from the mill and left to dry under ambient conditions overnight. XRPD analysis of the product showed it to be the same 1:1 cilostazol 4-hydroxybenzoic acid cocrystal obtained by the previous method. Approximately 5 mg (estimated by eye) of the product was placed in a glass vial and 500 μl of nitromethane was added. The sample was placed on a shaker at 50° C. for ca. 20 mins before being filtered into a clean vial. The vial was covered with film which was then pierced to allow slow evaporation and crystal formation. A suitable single crystal was isolated from the crystals which formed by this method.

The single crystal data and structure refinement parameters are reported in Table 7. FIG. 18 shows an ORTEP drawing of the asymmetric unit from the crystal structure of the cilostazol 4-hydroxybenzoic acid cocrystal showing the atom numbering scheme employed. Anisotropic atomic displacement ellipsoids for the non-hydrogen atoms are shown at the 50% probability level and hydrogen atoms are displayed as spheres of arbitrary radius. FIG. 19 shows the crystal packing of the 1:1 cilostazol 4-hydroxybenzoic acid cocrystal; the view is down the b-axis of the unit cell. The calculated XRPD pattern based on the single crystal data and structure for the 1:1 cilostazol 4-hydroxybenzoic acid cocrystal is shown in FIG. 20. It is also noted that there are some small temperature shifts in some of the peaks owing to the fact that the experimental XRPD pattern was collected at room temperature and the calculated XRPD pattern is derived from data collected at 100K. There are also small intensity differences owing to preferred orientation effects, present in the experimental pattern.

TABLE 7

| | |
|---|---|
| Molecular formula | $C_{27}H_{33}N_5O_5$ |
| Molecular weight | 507.58 |
| Crystal System | Monoclinic |
| Space Group | P21/n |
| Unit Cell Dimensions | a = 9.9992(2) Å |
| | b = 12.2374(2) Å |
| | c = 20.8210(3) Å |
| | α = 90.00° |
| | β = 101.975(2)° |
| | γ = 90.00° |
| Cell Volume | 2492.30(7) Å³ |
| Z | 4 |
| Temperature | 100 (2) K |
| Radiation Wavelength/type | 1.54178 Å/CuKα |
| Goodness of fit | 1.039 |
| R factor | 0.0349 |
| Morphology | Colourless prism |

3.4 DSC of 1:1 Cilostazol 4-Hydroxybenzoic Acid Cocrystal

The differential scanning calorimetry (DSC) trace, FIG. 21, shows a single endotherm with an onset temperature of 161.03° C. and a peak maximum of 161.64° C.

3.5 TGA of 1:1 Cilostazol 4-Hydroxybenzoic Acid Cocrystal

The thermal gravimetric analysis (TGA) trace, FIG. 22 shows no significant weight loss prior to degradation with 99.91% remaining at 170.0° C.

3.6 ¹H NMR Spectrum of 1:1 Cilostazol 4-Hydroxybenzoic Acid Cocrystal

The ¹H NMR spectrum of the 1:1 cilostazol 4-hydroxybenzoic acid cocrystal, shown in FIG. 23, displays the following peaks: ¹H NMR (400 MHz, d6-DMSO) δ: 12.45 (1H), 10.25 (1H), 9.92 (1H), 7.79 (2H), 6.78 (5H), 4.40 (1H), 3.96 (2H), 2.97 (2H), 2.82 (2H), 2.39 (2H), 1.66-2.00 (11H), 1.44 (2H), 1.26 (1H). The peak at 7.79 ppm in the ¹H NMR spectrum corresponds to two protons on the aromatic ring of the 4-hydroxybenzoic acid. Comparison of the integration of this peak with that at 4.40 ppm, which corresponds to one CH proton of the cyclohexyl ring of cilostazol, indicates that the cocrystal has an API:coformer stoichiometry of 1:1.

3.7 Karl Fischer Titration of the 1:1 Cilostazol 4-Hydroxybenzoic Acid Cocrystal Karl Fischer analysis of the 1:1 cilostazol 4-hydroxybenzoic acid cocrystal was carried out in triplicate and the results were 0.4%, 0.2% and 0.1% water content, confirming that the cocrystal is anhydrous.

3.8 Gravimetric Vapour Sorption (GVS) Analysis of the 1:1 Cilostazol 4-Hydroxybenzoic Acid Cocrystal The moisture sorption isotherm graph obtained for the 1:1 cilostazol 4-hydroxybenzoic acid cocrystal is shown in FIG. 24. The cocrystal was found to reversibly adsorb <0.08% w/w across the 0-90% relative humidity range at 25° C. under nitrogen. This shows that the cocrystal in not hygroscopic. XRPD analysis after completion of the isotherm confirmed that the cocrystal was unchanged.

3.9 Gram Scale Preparation of the 1:1 Cilostazol 4-Hydroxybenzoic Acid Cocrystal Cilostazol (6.00 g) was placed in a round bottom flask. 40 ml of a saturated solution of 4-hydroxybenzoic acid in methyl ethyl ketone was added. With stirring the resultant slurry was gradually heated using a water bath to approximately 60° C. After about 1 hour the water bath was removed and the slurry was stirred at room temperature for a further 20 hours before the product was filtered under vacuum and dried at 65° C. in an oven for 4 hours. XRPD analysis confirmed the product to be the 1:1 cilostazol 4-hydroxybenzoic acid cocrystal.

Example 4

1:1 Cilostazol 2,4 Dihydroxybenzoic Acid Cocrystal

4.1 Preparation of a 1:1 Cilostazol 2,4-Dihydroxybenzoic Acid Cocrystal

Cilostazol (300 mg) and 2,4-dihydroxybenzoic acid (125 mg) were weighed into a glass vial. Nitromethane (1.5 ml) was added to the vial. The resulting slurry was matured for 5 days (RT to 50° C. on an 8 hour cycle, heating to 50° C. for 4 hours and then cooling to RT for a further 4 hours). The product was then filtered under vacuum for ca. 1 hour before being allowed to dry under ambient conditions overnight.

4.2 XRPD Characterisation of the 1:1 Cilostazol 2,4-Dihydroxybenzoic Acid Cocrystal The experimental XRPD pattern of the 1:1 cilostazol 2,4-dihydroxybenzoic acid cocrystal is shown in FIG. 25. Table 8 lists the angles, °2θ±0.2°2θ, and d-spacing of the peaks identified in the XRPD pattern of FIG. 25. The entire list of peaks, or a subset thereof, may be sufficient to characterise the cocrystal. For example, the cocrystal may be characterised by at least five peaks selected from the peaks at 11.0, 13.0, 13.7, 15.5, 17.9, 19.1, 19.8, 20.9, 21.8 and 25.5 °2θ±0.2°2θ as well as by a XRPD pattern substantially similar to FIG. 25.

TABLE 8

| Angle 2-Theta ° | d value Angstrom | Intensity % % |
|---|---|---|
| 11.0 | 8.07 | 9.80 |
| 11.5 | 7.66 | 3.50 |
| 13.0 | 6.81 | 7.60 |
| 13.7 | 6.44 | 10.00 |
| 14.2 | 6.24 | 11.00 |
| 14.5 | 6.10 | 6.50 |
| 14.8 | 5.97 | 3.50 |
| 15.5 | 5.70 | 14.90 |
| 16.5 | 5.35 | 16.50 |
| 16.9 | 5.24 | 21.90 |
| 17.9 | 4.95 | 43.60 |
| 18.3 | 4.83 | 4.40 |
| 18.6 | 4.77 | 17.20 |
| 19.1 | 4.65 | 13.70 |
| 19.8 | 4.47 | 100.00 |
| 20.9 | 4.24 | 9.90 |
| 21.8 | 4.08 | 84.10 |
| 22.2 | 4.00 | 7.50 |
| 22.4 | 3.96 | 10.30 |
| 22.8 | 3.89 | 24.20 |
| 23.0 | 3.86 | 32.40 |
| 23.2 | 3.83 | 37.00 |
| 24.0 | 3.70 | 37.10 |
| 24.3 | 3.65 | 13.80 |
| 24.9 | 3.57 | 10.80 |
| 25.5 | 3.49 | 76.80 |
| 26.1 | 3.41 | 15.40 |
| 27.6 | 3.23 | 8.50 |
| 27.8 | 3.20 | 4.90 |
| 28.5 | 3.13 | 19.60 |
| 28.9 | 3.08 | 10.30 |
| 30.1 | 2.97 | 10.50 |
| 30.7 | 2.91 | 8.60 |
| 31.2 | 2.86 | 7.20 |
| 31.5 | 2.84 | 11.60 |
| 31.9 | 2.80 | 6.10 |
| 33.2 | 2.69 | 6.60 |
| 33.9 | 2.64 | 4.20 |
| 34.4 | 2.61 | 4.30 |
| 36.3 | 2.47 | 10.80 |
| 37.1 | 2.42 | 4.00 |
| 37.6 | 2.39 | 4.00 |
| 38.1 | 2.36 | 5.40 |
| 38.3 | 2.35 | 4.10 |
| 39.0 | 2.30 | 3.70 |
| 39.4 | 2.29 | 3.90 |

4.3 SCXRD Characterisation of a 1:1 Cilostazol 2,4-Diydroxybenzoic Acid Cocrystal The crystal used for single crystal structure determination was prepared as follows: Cilostazol (100 mg) and 2,4-dihydroxybenzoic acid (42 mg) were placed in a stainless steel ball mill. Water (2 drops) was added. The chemicals were ground together for 60 minutes at 20 Hz. The product was removed from the mill and left to dry under ambient conditions overnight. XRPD analysis of the product showed it to be the same 1:1 cilostazol 2,4-dihydroxybenzoic acid cocrystal obtained by the previous method. Approximately 5 mg (estimated by eye) of the product was placed in a glass vial and 500 μl of nitromethane was added. The sample was placed on a shaker at 50° C. for ca. 20 mins before being filtered into a clean vial. The vial was covered with film which was then pierced to allow slow evaporation and crystal formation. A suitable single crystal was isolated from the crystals which formed by this method.

The single crystal data and structure refinement parameters are reported in Table 9. FIG. 26 shows an ORTEP drawing of the asymmetric unit from the crystal structure of the cilostazol 2,4-dihydroxybenzoic acid cocrystal showing the atom numbering scheme employed. Anisotropic atomic displacement ellipsoids for the non-hydrogen atoms are shown at the 50% probability level and hydrogen atoms are displayed as spheres of arbitrary radius. FIG. 27 shows the crystal packing of the 1:1 cilostazol 2,4-dihydroxybenzoic acid cocrystal; the view is down the b-axis of the unit cell. The calculated XRPD pattern based on the single crystal data and structure for the 1:1 cilostazol 2,4-dihydroxybenzoic acid cocrystal is shown in FIG. 28. It is also noted that there are some small temperature shifts in some of the peaks owing to the fact that the experimental XRPD pattern was collected at room temperature and the calculated XRPD pattern is derived from data collected at 100K. There are also small intensity differences owing to preferred orientation effects, present in the experimental pattern.

TABLE 9

| | |
|---|---|
| Molecular formula | $C_{27}H_{33}N_5O_6$ |
| Molecular weight | 523.58 |
| Crystal System | Monoclinic |
| Space Group | P21/n |
| Unit Cell Dimensions | a = 9.8435(4) Å |
| | b = 12.2709(3) Å |
| | c = 21.3841(7) Å |
| | α = 90.00° |
| | β = 103.250(4)° |
| | γ = 90.00° |
| Cell Volume | 2514.19(14) Å$^3$ |
| Z | 4 |
| Temperature | 100 (2) K |
| Radiation Wavelength/type | 1.54178 Å/CuKα |
| Goodness of fit | 1.056 |
| R factor | 0.0296 |
| Morphology | Yellow prism |

4.4 DSC of 1:1 Cilostazol 2,4-Diydroxybenzoic Acid Cocrystal

The differential scanning calorimetry (DSC) trace, FIG. 29, shows a single endotherm with an onset temperature of 151.99° C. and a peak maximum of 152.97° C.

4.5 TGA of 1:1 Cilostazol 2,4-Dihydroxybenzoic Acid Cocrystal

The thermal gravimetric analysis (TGA) trace, FIG. 30, shows no significant weight loss prior to degradation with 99.54% remaining at 157.5° C.

4.6 $^1$H NMR Spectrum of 1:1 Cilostazol 2,4-Dihydroxybenzoic Acid Cocrystal The $^1$H NMR spectrum of the 1:1 cilostazol 2,4-dihydroxybenzoic acid cocrystal, shown in FIG. 31, displays the following peaks: $^1$H NMR (400 MHz, d6-DMSO) δ: 11.44 (1H), 10.39 (1H), 9.92 (1H), 7.62 (1H), 6.76 (3H), 6.34 (1H), 6.26 (1H), 4.40 (1H), 3.96 (2H), 2.97 (2H), 2.82 (2H), 2.39 (2H), 1.64-2.00 (11H), 1.44 (2H), 1.26 (1H). The peak at 6.26 ppm in the $^1$H NMR spectrum corresponds to one proton on the aromatic ring of the 2,4-dihydroxybenzoic acid. Comparison of the integration of this peak with that at 4.40 ppm, which corresponds to one CH proton of the cyclohexyl ring of cilostazol, indicates that the cocrystal has an API:coformer stoichiometry of 1:1.

4.7 Karl Fischer Titration of the 1:1 Cilostazol 2,4-Dihydroxybenzoic Acid Cocrystal Karl Fischer analysis of the 1:1 cilostazol 2,4-dihydroxybenzoic acid cocrystal was carried out in triplicate and the results were 0.1%, 0.3% and 0.3% water content, confirming that the cocrystal is anhydrous.

4.8 Gravimetric Vapour Sorption (GVS) Analysis of the 1:1 Cilostazol 2,4-Dihydroxybenzoic Acid Cocrystal The moisture sorption isotherm graph obtained for the 1:1 cilostazol 2,4-dihydroxybenzoic acid cocrystal is shown in FIG. 32. The cocrystal was found to reversibly adsorb <0.3% w/w across the 0-90% relative humidity range at 25° C. under nitrogen. This shows that the cocrystal in not hygroscopic. XRPD analysis after completion of the isotherm confirmed that the cocrystal was unchanged.

4.9 Gram Scale Preparation of the 1:1 Cilostazol 2,4-Hydroxybenzoic Acid Cocrystal Cilostazol (6.00 g) was placed in a round bottom flask. 40 ml of a saturated solution of 2,4-dihydroxybenzoic acid in methyl ethyl ketone was added. With stirring the resultant slurry was gradually heated using a water bath to approximately 60° C. After about 1 hour the water bath was removed and the slurry was stirred at room temperature for a further 20 hours before the product was filtered under vacuum and dried at 65° C. in an oven for 4 hours. XRPD analysis confirmed the product to be the 1:1 cilostazol 2,4-dihydroxybenzoic acid cocrystal.

Example 5

Pharmacokinetic Study

5.1 Study Design

The study was designed to compare the pharmacokinetic profiles of the 1:1 cilostazol gentisic acid cocrystal (prepared as described in Example 1.9), the 1:1 cilostazol 4-hydroxybenzoic acid cocrystal (prepared as described in Example 3.9) and the 1:1 cilostazol 2,4-dihydroxybenzoic acid cocrystal (prepared as in Example 4.9) with that of the crystalline cilostazol following oral administration under fasted conditions at a dosage level corresponding to 100 mg cilostazol in beagle dogs. A crossover study was carried out using 5 male beagle dogs with a washout period of 5 days between each treatment. Prior to dosing, the dogs were fasted overnight. The capsules were accurately filled with the amount of cilostazol or the corresponding cocrystal that was equivalent to 100 mg cilostazol. The capsules were orally administered to the dogs followed by about 10 mL of water. Food (about 250 g) was provided 4 hours post-dose to all animals.

5.2 Blood Sample Collection

Blood samples were collected at pre-dose, 15 and 30 minutes, and 1, 2, 3, 4, 6, 8, 10, 12 and 24 hour post-dose (12 time points) following oral dose administration. Approximately 0.8 ml of whole blood was withdrawn from the cephalic vein and placed in labelled tubes containing sodium heparin as anticoagulant (20 μL of 400 IU/mL sodium heparin solution per mL of blood). Plasma was separated by centrifuging the whole blood at about 2500 g for 10 minutes at 4° C. Separated plasma was stored below −70° C. until analysis.

5.3 Bioanalysis

A fit for purpose LC-MS/MS method was used for the determination of the cilostazol concentrations in the plasma samples. Pharmacokinetic parameters from individual samples were calculated using the non-compartmental analysis tool of the WinNonlin® software (version 5.2). The area under the plasma concentration curve (AUC) was calculated using the linear trapezoidal rule. Peak plasma concentration ($C_{max}$) and the time taken to reach the peak plasma concentration ($T_{max}$) were the observed values.

5.4 Pharmacokinetic Results

Table 10 shows the mean $C_{max}$ and AUC values for each sample as well as the median $T_{max}$ value. The mean blood plasma concentration-time profiles for all four test samples are shown in FIG. 33.

TABLE 10

| Test Item | $C_{max}$ (ng/mL) | $T_{max}$ (h) | AUC (ng · h/mL) |
|---|---|---|---|
| 1:1 Cilostazol Gentisic Acid Cocrystal | 471.42 | 1.00 | 1216.37 |
| 1:1 Cilostazol 4-Hydroxybenzoic Acid Cocrystal | 1361.15 | 1.00 | 3944.94 |
| 1:1 Cilostazol 2,4-Dihydroxybenzoic Acid Cocrystal | 1189.84 | 0.50 | 3326.18 |
| Cilostazol | 81.54 | 2.00 | 370.95 |

The claimed invention is:

1. A cilostazol cocrystal selected from a 1:1 cilostazol gentisic acid cocrystal, a 1:1:1 cilostazol gentisic acid $H_2O$ cocrystal, a 1:1 cilostazol 4-hydroxybenzoic acid cocrystal, and a 1:1 cilostazol 2,4-dihydroxybenzoic acid cocrystal.

2. A pharmaceutical composition comprising at least one cilostazol cocrystal of claim 1 and a pharmaceutically acceptable carrier.

3. A cilostazol composition selected from a 1:1 cilostazol gentisic acid composition, a 1:1:1 cilostazol gentisic acid $H_2O$ composition, a 1:1 cilostazol 4-hydroxybenzoic acid composition, and a 1:1 cilostazol 2,4-dihydroxybenzoic acid composition.

4. A pharmaceutical composition comprising at least one cilostazol composition of claim 3 and a pharmaceutically acceptable carrier.

5. A 1:1 cilostazol gentisic acid cocrystal characterized by at least one of:
a powder X-ray diffraction pattern having at least five peaks selected from 3.5, 6.9, 10.4, 16.5, 17.3 and 17.8, 20.5, 22.0, 23.0, 23.6 °2θ±0.2°2θ,
a powder X-ray diffraction pattern substantially similar to FIG. 1,
a P-1 space group, and
unit cell dimensions of a=6.5528(3) Å, b=8.0562(3) Å, c=25.5472(12) Å, α=89.086(4)°, β=83.993(4)°, and γ=73.079(4)° at a temperature of 100 K.

6. A 1:1:1 cilostazol gentisic acid $H_2O$ cocrystal characterized by at least one of:
a powder X-ray diffraction pattern having at least five peaks selected from 5.1, 7.9, 10.1, 12.6, 14.8, 16.9, 18.2, 22.8, 24.9 and 25.5 °2θ±0.2°2θ,
a powder X-ray diffraction pattern substantially similar to FIG. 9,
a P21/n space group, and
unit cell dimensions of a=6.6287(3) Å, b=34.531(2) Å, c=11.6203(8) Å, α=90.00°, β=90.155(6)°, γ=90.00° at a temperature of 120 K.

7. A 1:1 cilostazol 4-hydroxybenzoic acid cocrystal characterized by at least one of:
a powder X-ray diffraction pattern having at least five peaks selected from 11.2, 12.8, 14.3, 15.7, 18.0, 19.3, 20.9, 21.5, 22.0 and 26.0 °2θ±0.2°2θ,
a powder X-ray diffraction pattern substantially similar to FIG. 17,
a P21/n space group, and
unit cell dimensions of a=9.9992(2) Å, b=12.2374(2) Å, c=20.8210(3) Å, α=90.00°, β=101.975(2)°, γ=90.00° at a temperature of 100 K.

8. A 1:1 cilostazol 2,4-dihydroxybenzoic acid cocrystal characterized by at least one of:
a powder X-ray diffraction pattern having at least five peaks selected from 11.0, 13.0, 13.7, 15.5, 17.9, 19.1, 19.8, 20.9, 21.8 and 25.5 °2θ±0.2°2θ,
a powder X-ray diffraction pattern substantially similar to FIG. 25,
a P21/n space group, and
unit cell dimensions of a=9.8435(4) Å, b=12.2709(3) Å, c=21.3841(7) Å, α=90.00°, β=103.250(4)°, γ=90.00° at a temperature of 100 K.

9. A pharmaceutical composition comprising 1:1 cilostazol gentisic acid cocrystal of claim 5 and a pharmaceutically acceptable carrier.

10. A pharmaceutical composition comprising 1:1:1 cilostazol gentisic acid $H_2O$ cocrystal of claim 6 and a pharmaceutically acceptable carrier.

11. A pharmaceutical composition comprising 1:1 cilostazol 4-hydroxybenzoic acid cocrystal of claim 7 and a pharmaceutically acceptable carrier.

12. A pharmaceutical composition comprising 1:1 cilostazol 2,4-dihydroxybenzoic acid cocrystal of claim 8 and a pharmaceutically acceptable carrier.

* * * * *